United States Patent
Fleenor et al.

(10) Patent No.: US 7,166,102 B2
(45) Date of Patent: *Jan. 23, 2007

(54) SELF-LIMITING ELECTROSURGICAL RETURN ELECTRODE

(75) Inventors: Richard P. Fleenor, Englewood, CO (US); David B. Kieda, Salt Lake City, UT (US); James D. Isaacson, Salt Lake City, UT (US); Paul R. Borgmeier, Salt Lake City, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 664 days.

This patent is subject to a terminal disclaimer.

(21) Appl. No.: 10/142,253

(22) Filed: May 9, 2002

(65) Prior Publication Data

US 2003/0040741 A1 Feb. 27, 2003

Related U.S. Application Data

(63) Continuation-in-part of application No. 09/769,025, filed on Jan. 24, 2001, now Pat. No. 6,582,424, and a continuation-in-part of application No. 09/569,998, filed on May 12, 2000, now Pat. No. 6,454,764, and a continuation-in-part of application No. 09/435,498, filed on Nov. 6, 1999, now Pat. No. 6,214,000, and a continuation-in-part of application No. 09/201,998, filed on Nov. 30, 1998, now Pat. No. 6,083,221, and a continuation-in-part of application No. 08/741,468, filed on Oct. 30, 1996, now abandoned, and a continuation-in-part of application No. 08/741,469, filed on Oct. 30, 1996, now Pat. No. 6,053,910.

(51) Int. Cl.
*A61B 18/16* (2006.01)

(52) U.S. Cl. .............. 606/32; 606/35; 607/152; 128/908

(58) Field of Classification Search .......... 606/32, 606/35, 39; 607/152; 128/908
See application file for complete search history.

(56) References Cited

U.S. PATENT DOCUMENTS

| 3,089,496 A | 5/1963 | Degelman | 128/303.14 |
| 3,543,760 A | 12/1970 | Bolduc | 128/416 |
| 3,720,209 A | 3/1973 | Bolduc | 128/2.06 E |

(Continued)

FOREIGN PATENT DOCUMENTS

| GB | 1 480 736 | 7/1977 |
| GB | 2 052 269 | 1/1981 |
| JP | S55-168317 | 12/1980 |
| JP | S57-154409 | 9/1982 |
| JP | S63-54148 | 3/1998 |

OTHER PUBLICATIONS

Wald, et al., "Accidental Burns Associated With Electrocautery," JAMA, Aug. 16, 1971, vol. 217, No. 7, pp. 916–921.

*Primary Examiner*—Lee S. Cohen
(74) *Attorney, Agent, or Firm*—Workman Nydegger

(57) ABSTRACT

A removable semi-insulating sheet for use in self-limiting electrosurgical return semi-insulating sheet for use with electrosurgery. Through the selection of impedance characteristics for the electrode materials of the principal body of the semi-insulating sheet, and through tailoring of semi-insulating sheet geometries, the return electrode of the present invention is self-regulating and self-limiting as to current density and temperature rise so as to prevent patient trauma. The semi-insulating sheet has an effective bulk impedance equal to or greater than about 4,000 Ω·cm. The effective bulk impedance of the sheet may arise from resistive components, capacitive components, inductive components, or combinations thereof. The configuration of the presently described return electrode allows the electrode to self-limit the electrode's current densities, thereby preventing burning of a patient during surgery.

31 Claims, 9 Drawing Sheets

U.S. PATENT DOCUMENTS

| | | | |
|---|---|---|---|
| 3,848,600 A | 11/1974 | Patrick, Jr. et al. | 128/303.13 |
| 4,088,133 A | 5/1978 | Twentier | 128/303.13 |
| 4,092,985 A | 6/1978 | Kaufman | 128/303.13 |
| 4,094,320 A | 6/1978 | Newton et al. | 128/303.14 |
| 4,117,846 A | 10/1978 | Williams | 128/303.13 |
| 4,166,465 A | 9/1979 | Esty et al. | 128/303.13 |
| 4,200,104 A | 4/1980 | Harris | 128/303.14 |
| 4,207,904 A | 6/1980 | Greene | 128/798 |
| 4,226,247 A | 10/1980 | Hauser et al. | 128/641 |
| 4,231,372 A | 11/1980 | Newton | 128/303.13 |
| 4,237,886 A | 12/1980 | Sakurada et al. | 128/303.13 |
| 4,237,887 A | 12/1980 | Gonser | 128/303.14 |
| 4,267,840 A | 5/1981 | Lazar et al. | 128/303.13 |
| 4,304,235 A | 12/1981 | Kaufman | 128/303.13 |
| 4,384,582 A | 5/1983 | Watt | 128/303.13 |
| 4,387,714 A | 6/1983 | Geddes et al. | 128/303.13 |
| 4,669,468 A | 6/1987 | Cartmell et al. | 128/303.13 |
| 4,770,173 A | 9/1988 | Feucht et al. | 128/303.13 |
| 4,799,480 A | 1/1989 | Abraham et al. | 128/303.13 |
| 5,352,315 A | 10/1994 | Carrier et al. | 156/267 |
| 5,354,790 A | 10/1994 | Keusch et al. | |
| 5,520,683 A | 5/1996 | Subramaniam et al. | 606/32 |
| 5,836,942 A | 11/1998 | Netherly et al. | 606/32 |
| 6,053,910 A | 4/2000 | Fleenor | |
| 6,083,221 A | 7/2000 | Fleenor et al. | |
| 6,454,764 B1 * | 9/2002 | Fleenor et al. | 606/32 |

* cited by examiner

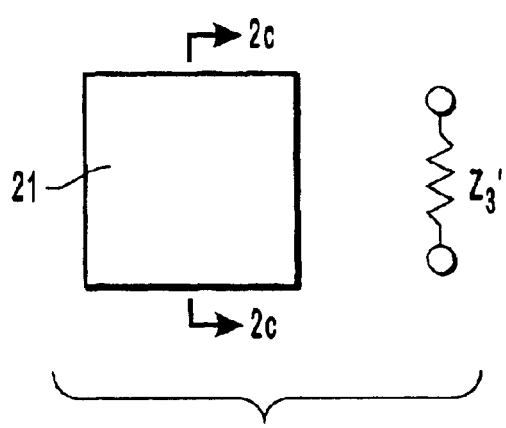
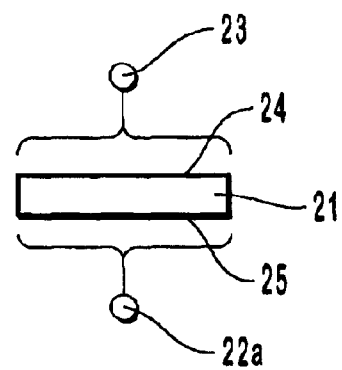
FIG. 2B                FIG. 2C
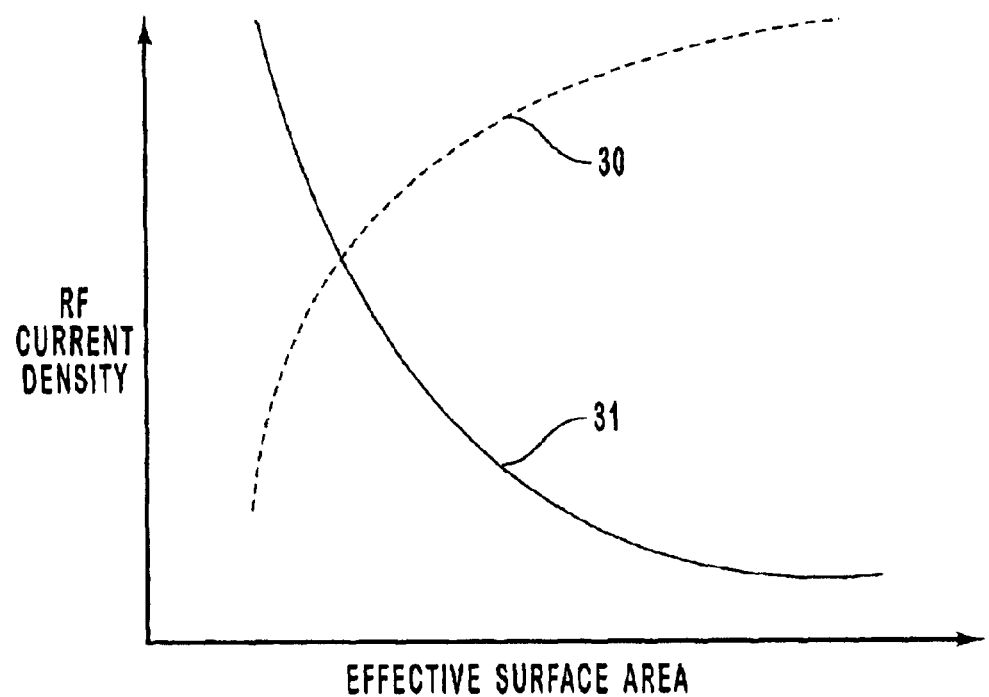
FIG. 3

SELF-LIMITING ELECTROSURGICAL RETURN ELECTRODE

CROSS-REFERENCE TO RELATED APPLICATIONS

This is continuation-in-part application of U.S. patent application Ser. No. 09/569,998 filed May 12, 2000, now U.S. Pat. No. 6,454,764 and entitled "Self-limiting electrosurgical return electrode," that is a continuation-in-part application of U.S. patent application Ser. No. 09/201,998, filed Nov. 30, 1998 now U.S. Pat. No. 6,083,221, and entitled "Resistive Reusable Electrosurgical Return Electrode," that is a continuation-in-part application of U.S. patent application Ser. No. 08/741,468, filed Oct. 30, 1996, now abandoned and entitled "Reusable Electrosurgical Return Pad." This is a continuation-in-part application of U.S. patent application Ser. No. 09/769,025, filed Jan. 24, 2001, now U.S. Pat. No. 6,582,424 and entitled "Capacitive Reusable Electrosurgical Return Electrode", that is a continuation-in-part application of U.S. patent application Ser. No. 09/435,498, filed Nov. 6, 1999, now U.S. Pat. No. 6,214,000 and entitled "Capacitive Reusable Electrosurgical Return Electrode", and U.S. patent application Ser. No. 08/741,469, filed Oct. 30, 1996, now U.S. Pat. No. 6,053,910 and entitled "Capacitive Reusable Electrosurgical Return Electrode," the disclosures of which are incorporated by this reference.

BACKGROUND OF THE INVENTION

1. The Field of the Invention

This invention relates to electrosurgery and, more particularly, to a semi-insulating sheet or member adapted for providing effective and safe electrosurgical energy return without conducting or dielectric gels and for providing such safe electrosurgical energy return using a separate electrically conductive element.

2. The Relevant Technology

As is known to those skilled in the art, modern surgical techniques typically employ radio frequency (RF) power to cut tissue and coagulate bleeding encountered in performing surgical procedures. For historical perspective and details of such techniques, reference is made to U.S. Pat. No. 4,936,842, issued to D'Amelio et al., and entitled "Electroprobe Apparatus," the disclosure of which is incorporated by this reference.

As is known to those skilled in the medical arts, electrosurgery is widely used and offers many advantages including the use of a single surgical instrument for both cutting and coagulation. Every monopolar electrosurgical generator system must have an active electrode that is applied by the surgeon to the patient at the surgical site to perform surgery and an electrical connector from the patient back to the generator. The active electrode at the point of contact with the patient must be small in size to produce a high current density in order to produce a surgical effect of cutting or coagulating tissue. The return electrode, which carries the same current as the active electrode, must be large enough in effective surface area at the point of communication with the patient such that a low density current flows from the patient to the return electrode. In the event that a relatively high current density is produced at the return electrode, the temperature of the patient's skin and tissue will rise in this area and can result in an undesirable patient burn.

In 1985, the Emergency Care Research Institute, a well-known medical testing agency, published the results of testing it had conducted on electrosurgical return electrode site burns, reporting that the heating of body tissue to the threshold of necrosis occurs when the current density exceeds 100 milliamperes per square centimeter.

The Association for the Advancement of Medical Instrumentation ("AAMI") has published standards that require that the maximum patient surface tissue temperature adjacent an electrosurgical return electrode shall not rise more than six degrees (6°) Celsius under stated test conditions.

Over the past twenty years, industry has developed products in response to the medical need for a safer return electrode in two major ways. First, they went from a small, about 12×7 inches, flat stainless steel plate coated with a conductive gel placed under the patient's buttocks, thigh, shoulders, or any location where gravity can ensure adequate contact area to a flexible electrode. These flexible electrodes, which are generally about the same size as the stainless steel plates, are coated with a conductive or dielectric polymer and have an adhesive border on them so they will remain attached to the patient without the aid of gravity, and are disposed of after use. By the early 1980's, most hospitals in the United States had switched over to using this type of return electrode. These return electrodes are an improvement over the old steel plates and resulted in fewer patient return electrode burns but have resulted in additional surgical costs in the United States of several tens of millions of dollars each year. Even with this improvement, hospitals were still experiencing some patient burns caused by electrodes that would accidentally fall off or partially separate from the patient during surgery.

Subsequently, there was proposed a further improvement, an Electrode Contact a Quality Monitoring System that would monitor the contact area of the electrode that is in contact with the patient and turn off the electrosurgical generator whenever there was insufficient contact area. Such circuits are shown, for example, in U.S. Pat. No. 4,231,372, issued to Newton, and entitled "Safety Monitoring Circuit for Electrosurgical Unit," the disclosure of which is incorporated by this reference. This system has resulted in additional reduction in patient return electrode burns, but requires a special disposable electrode and an added circuit in the generator that drives the cost per procedure even higher. Fifteen years after this system was first introduced, fewer than 40 percent of all the surgical operations performed in the United States use this system because of its high costs.

BRIEF SUMMARY OF THE INVENTION

The present invention overcomes the problems of the prior art by providing a semi-insulating sheet or member that may be used in connection with a separate electrically conducting element coupled to a electrical connector of the electrosurgical generator. This combination collectively acts as a return electrode that eliminates patient burns without the need for expensive disposable electrodes and monitoring circuits associated with specialized RF generators.

Briefly, the semi-insulating sheet or member provides self-limiting characteristics when used in connection with an electrically conducting element such as a metal table, metal chair, or other existing work surface. The inclusion of the semi-insulating sheet or member converts such electrically conducting element into an improved electrode with desirable self-limiting characteristic of an improved return electrode. According to one embodiment of the invention hereof, the semi-insulating sheet or member, when used with an electrically conducting element, provides an effective surface area that is larger than other return electrodes that have been disclosed or used in surgery previously. The surface is so large and so adapted for positioning relative to the body of a patient that the combination of the semi-insulating sheet and the electrically conducting element eliminates the need for conductive or dielectric gels.

The semi-insulating sheet or member is removable and configured to cooperate with any electrically conducting element to act as a return electrode. Thus, any electrically conducting work surface can be transformed, by use of the semi-insulating sheet and the addition of an electrical connection between the existing electrically conducting work surface and an electrosurgical generator, into a return electrode having the desired self-limiting characteristics. Moreover, the semi-insulating sheet or member is of a material that is readily washable and/or sterilizable so as to facilitate easy and rapid conditioning for repeated reuse.

Generally, the sheet employs geometries and materials whose impedance characteristics, at typically used electrosurgical frequencies, are such that the sheet or member self-limits current densities (and corresponding temperature rises) to safe thresholds, should the effective area of the working surface of the electrode be reduced below otherwise desirable levels. Accordingly, the need for the foregoing expensive monitoring circuits in specialized RF generators is eliminated. Additionally, the need to provide a complete return electrode is also eliminated, further reducing the costs of providing the benefits of an improved electrode. Thus, an improved return electrode is provided by merely supplying a semi-insulating sheet and an electrical connector attachable to the separate electrically conducting element, which can then be combined with such an electrically conducting element to provide an electrosurgical return electrode with the desired characteristics.

In an embodiment of the present invention, the electrosurgical return electrode, i.e., combination of the semi-insulating sheet or member and the electrically conducting element, is made sufficiently large to present sufficiently low electrical impedance and low current densities at typical electrosurgery frequencies used in medical procedures to reduce the possibility of excessive temperature elevation in adjacent patient tissue, (i.e., by maintaining temperature ("T") rise below six degrees (6° Celsius) thereby avoiding tissue necrosis or other undesired patient trauma. Therefore, the working surface of the semi-insulating sheet or member (the surface that is in contact with or in close proximity to the patient) is made sufficiently large in area so that in normal use, current flow will not be reduced to a point where it impedes the surgeon's ability to perform surgery at the surgical site.

In accordance with one embodiment of the invention, the semi-insulating sheet or member has sufficient dielectric properties that, when used in connection with the electrically conducting element, provides sufficient impedance to limit the passage of current therethrough to safe values. In one embodiment, the desired impedance characteristics are achieved by imparting controlled electrical conductivity to the sheet by the inclusion therein of electrically conductive materials such as conductive threads or carbon black.

In accordance with yet another embodiment of the invention, a moisture impervious working surface is provided for positioning adjacent an adjoining surface of the body of a patient, thus facilitating cleansing and reuse of the semi-insulating sheet. This moisture impervious working surface is made resistant to normally encountered cleaning, disinfecting, and sterilizing agents, thus further facilitating cleansing and reuse.

In another embodiment, a sleeve is provided for cooperative use with the semi-insulating sheet or member, thus protecting the sheet from inadvertent damage that might occur, for example, from damage from accidental cutting from a conventional surgical scalpel. In another embodiment, a protective flange is coupled to the semi-insulating sheet or member, such that the protective flange substantially covers the electrically conducting working surface to prevent accidental contact with the electrically conducting element.

In another embodiment, a covering is provided to enclose the electrically conducting element, such as a surgical table or metal plate, thus, protecting the patient and the user from accidentally touching the electrically conducting element, which may result in serious injury to either patient or user. In another embodiment, the semi-insulating layer is form-fitted to the operating table on which the electrosurgical procedure is to be performed, thus facilitating realization of other features of the invention. In yet another embodiment, the semi-insulating sheet or member has the form of an envelope for enclosing the separate conducting element.

In accordance with yet another embodiment of the invention, the electrical impedance of the materials in the sheet or member and adjacent to the working surface of the electrode is sufficiently elevated so as to limit current density at the working surface to a level below the threshold of patient tissue trauma. Consequently, this provides a self-limiting characteristic to prevent patient trauma in the event of accidental reduction of the effective working surface of the electrode.

Additional features and advantages of the invention will be set forth in the description which follows, and in part will be obvious from the description, or may be learned by the practice of the invention. These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 2B is an enlargement of a segment of the electrosurgical return electrode of FIG. 2A;

FIG. 2C is a cross section taken along the section lines 2C—2C of FIG. 2B and illustrating the effective circuit impedance represented by the segment of 2B;

FIG. 3 is a chart illustrating in graphical form the relationships between effective surface area of the return electrode and the effective radio frequency current density developed at the electrode;

DETAILED DESCRIPTION OF THE EXEMPLARY EMBODIMENTS

Figure 1:
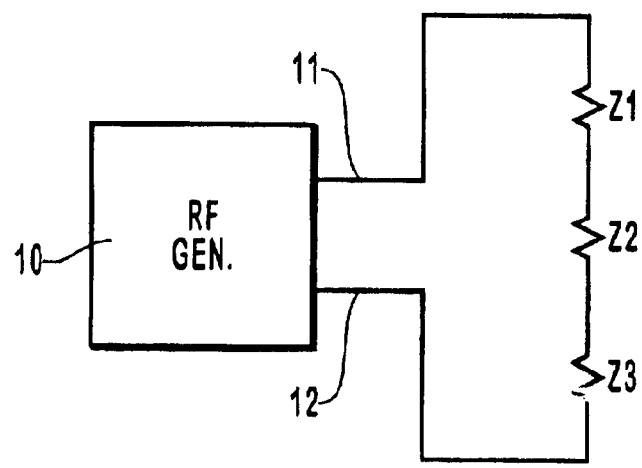
FIG. 1 is a simplified electrical schematic diagram illustrating typical impedances effectively included in the operative path of radio frequency current flow as presented to an electrosurgical generator during an operative procedure.

Now turning to the drawings, and more particularly FIG. 1, therefore it will be seen to depict a simplified electrical schematic diagram illustrating typical impedances effectively included in the operative path of radio frequency current flow as presented to an electrosurgical generator during an operative procedure. There, it will be seen are conventional radio frequency electrical power generator 10, such as but not limited to constant power, voltage, and/or current or variable power, voltage and/or current. Connected to electrical power generator 10 are conventional electrical connectors 11 and 12, which respectively connect the generator 10 to the surgeon's implement, represented by impedance $z_1$ and an electrosurgical return electrode represented by impedance $z_3$. Impedance $z_2$ is provided to represent the impedance presented by the patient's tissue lying between the operation site and the return electrode. Electrical connectors 11 and 12 are representative of one illustrative structure that is capable of performing the function of connecting means for making electrical connection to the semi-insulating sheet or member and/or the electrically conducting element. It may be appreciated by one skilled in the art, that various other structures are appropriate and capable of performing the desired function, in light of the teaching contained herein.

Figure 2A:
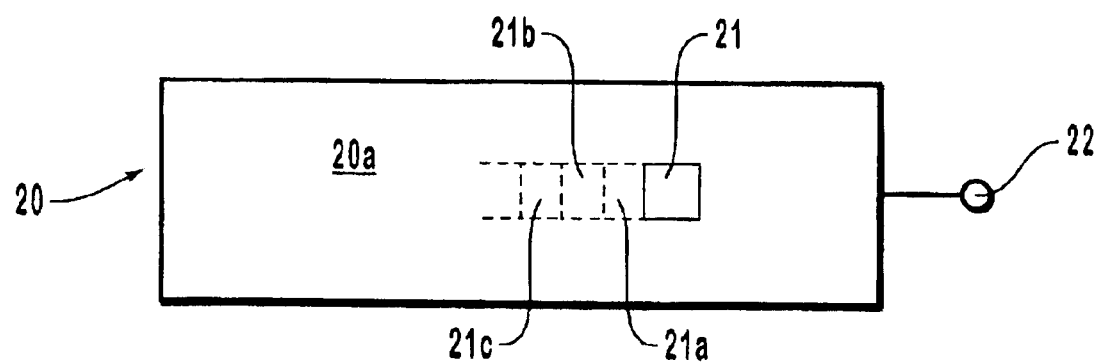
FIG. 2A is a top view of a wide-area distributed electrosurgical return electrode illustrating the principles of the invention.

Although the diagram of FIG. 2A is simplified and generally considers circuit elements in terms of the principal resistances, including the reactances contributed by the surgical instrument, the patient's body and the return electrode, so as to clearly and succinctly illustrate principles of the invention, it should be understood that in reality certain other parameters would be encountered, parameters such as distributed inductance and distributed capacitance which, for purposes of clarity in illustration of the principles hereof, are deemed relatively small and so not considered at this point in this description. However, as set forth below, in one embodiment when an insulating sleeve is interposed between the electrode and the body of a patient, a significant element of capacitive reactance may be included in the impedance of $z_3$. It should also be noted that FIGS. 1–11 are intentionally simplified so as to present the principles of the invention succinctly, with a more rigorous and complete discussion being presented in connection with FIGS. 12–18.

The initial embodiment, hereof, is that of an electrode, i.e., a semi-insulating sheet or member and an electrically conducting element, operating in a combined resistive, capacitive, and/or inductive mode. Accordingly, if the relatively small stray capacitive and inductive reactances are disregarded, the total effective impedance of the circuit will be equal to the sum of the individual impedances $z_1$, $z_2$ and $z_3$; and since essentially the same current will pass through all three, the voltage generated by RF generator 10 will be distributed across impedances $z_1$, $z_2$ and $Z_3$ in direct proportion to their respective values. Thus, the energy released in each of such components will also be directly proportional to their values.

Since it is desired that developed energy be concentrated in the region where the surgeon's implement contacts the patient's tissue, it is desirable that the resistive component of the impedance represented by $z_1$ be substantial and that current passing therethrough (and consequent energy release) be concentrated in a very small region. The latter is accomplished by making the region of contact with the patient at the operative site very small.

It is known that, in contrast with the foregoing series circuit, components of combined resistive and capacitive reactance, when connected in parallel, present a total effective impedance that is given by the formula:

$$Z_{\text{eff}} = \frac{1}{\frac{1}{Z_1} + \frac{1}{Z_2} + \frac{1}{Z_3} + \frac{1}{Z_4} + \frac{1}{Z_5} + \frac{1}{Z_6}} \tag{1}$$

Thus, if 100 similar impedances, each of 100 ohms, were connected in parallel, the effective impedance $Z_{\text{eff}}$ would equal one ohm. In the event that half of such impedances were effectively disconnected, the remaining effective impedance would be two ohms, and if only one of the impedances were active in the circuit, the remaining effective impedance would be 100 ohms. The significance of these considerations and their employment to render the electrode hereof self-limiting and fail-safe will be evident from the following description of the elements illustrated in FIGS. 2A, 2B, 2C and 3.

Now turning to FIG. 2A, there will be seen a schematic representation of the top view of a wide-area distributed electrosurgical return electrode 20 that will be used to describe the principles of the self-limiting characteristics. Although reference is made to electrosurgical return electrode 20 in the discussion of embodiments of the present invention, it can be understood that a semi-insulating sheet or member and an electrically conducting element, in combination, form an electrosurgical return electrode.

At the right hand side of FIG. 2A, there is shown an electrical connection terminal 22 to facilitate connection to an electrical return connector. A surface 20a of return electrode 20, i.e., a surface of a semi-insulating sheet or member, can be smooth and homogeneous and includes a thin resistive and/or dielectric layer 21a (FIG. 2C). Alternatively, surface 20a includes a semi-insulating sheet or member of return electrode 20 which may include a capacitive and/or inductive layer, depending on the particular operation of the semi-insulating sheet or member. For instructional purposes of this description and to aid in the mathematical modeling of return electrode 20, electrode 20 may be thought of as including a plurality of uniformly-sized regions or segments as represented by regions 21, 21a, 21b, 21c . . . 21n. It will be appreciated by one skilled in the art, however, that return electrode may or may not include discontinuous regions or segment. For instance, in one embodiment electrode 20 has continuous segments.

Region/segment 21 is shown larger in FIG. 2B in order to be similar in scale to the resistive impedance $z_3'$ it represents. It thus will now be evident that each of the segments of electrode 20 corresponding to segments 21 . . . 21 n inherently has the capability of presenting an impedance similar to that of impedance $z_3'$. However, the number of such segments that are effectively active in parallel within the circuit is a direct function of the surface area of the patient that overlies the electrode. Thus, in the case of a large supine patient whose body is in effective contact with 50 percent (50%) of the upper surface of the electrode, 50 percent of the segments corresponding to segments 21–21n will be effectively paralleled in the circuit to form an impedance represented by impedance $z_3$ of FIG. 1; and, accordingly, if electrode 20 contains 100 segments of 100 ohms each, the effective impedance operatively presented by the effective 50 percent of the electrode elements would be two ohms. Since two ohms is very small compared with the impedance represented by elements $z_1$ and $Z_2$, very little energy is dissipated at the region of contact between the patient and the electrode, and due also to the relatively large effective working area of the electrode, current density, and temperature elevation are maintained below the danger thresholds mentioned above.

Now, if for any reason, the effective contact area between the patient and electrode were to be reduced to the surface of only one of the segments 21–21n, then the effective impedance (combined capacitive reactance and resistance in the example under consideration) would increase to 100 ohms; and at some point of reduction in contact area, the effective impedance would rise to a level relative to the impedance presented at the site of the electrosurgical instrument so as to diminish the electrosurgical effect of the surgical instrument or otherwise prevent effective use of the instrument by the surgeon, thus signaling the surgeon that the patient should be repositioned so as to present a greater surface area in contact with the return electrode. At the same time, the total circuit impedance would be increased so that the total current that would flow if the surgeon attempted to employ his instrument without repositioning the patient would be reduced to a value below that which would cause undesired trauma to the patient. Accordingly, there is provided a self-limiting feature that enhances safety in use without the need for the aforementioned separate circuit monitoring and control circuits.

FIG. 2C is a cross section taken along the section lines 2C—2C of FIG. 2B and illustrates the effective circuit impedance $z_3'$ represented by the segment 21 of 2B. There, in FIG. 2C are seen small segment 21 with its upper patient-contacting surface 24 represented electrically by terminal 23 and its lower surface 25 represented by electrical terminal 22a. For the purpose of this description (and in order to present the principles underlying this embodiment clearly), the impedance $z_3'$ may be thought of as existing between terminals 23 and 22a. Of course, it will be evident to those skilled in the art that in an embodiment in which the electrically conducting element is a thin but highly conductive layer each of the impedances represented by the remaining segments are connected at their lower extremities in parallel to terminal 22; whereas, if such element does not have such highly conductive properties, then, in addition to the impedance represented by the material lying between the upper and lower regions of each segment, there will be an additional impedance (not shown) that is represented by the material through which current would have to pass transversely or laterally through the electrode in order to get to terminal 22.

It should now be evident that if lateral impedance is minimized by provision of the aforementioned thin conducting layer, or if the effective conductivity at the lower part of the material of region 21 is otherwise increased, the effective impedance presented by the return electrode will be inversely proportional to the effective upper surface of the electrode that is in contact with a patient.

FIG. 3 is a chart generally illustrating in graphic form the relationships between the effective surface area of the return electrode and the effective radio frequency current densities developed at the electrode. However, before proceeding to a consideration of such chart, it should be noted that the chart is simplified so as to illustrate the principles of a self-limiting return electrode and does not represent actual data that may vary substantially. In FIG. 3 there is seen a plot of RF Current Density versus Electrode Effective Surface Area, the latter (as should now be evident to those skilled in the art) being that part of the surface of the return electrode that makes effective electrical contact with the body of a patient. As would be expected from the foregoing discussion, when the effective area is large, the current at the surgeon's implement is high (dashed graph line 30) and the corresponding current density across the return electrode is very low (solid graph line 31). This is, of course, the condition desired for conducting surgery. However, if we assume constant current throughout the circuit, as the effective surface area decreases, the current density across the return electrode (solid graph line 31) increases with a corresponding decrease in the current at the surgeon's instrument (dashed graph line 30). When the effective surface area declines to some predetermined point, there will remain insufficient current at the surgical instrument to effectively conduct surgery.

It may be appreciated by one skilled in the art that the change in current density and available current to the surgeon may or may not occur simultaneously with the variations in effective surface area. Various embodiments of the present invention may have substantially simultaneous changes in current density and available current, while other embodiments of the present invention may include a lag period therebetween.

The parameters selected for the materials and electrode dimensions are chosen so that current density and corresponding tissue temperature elevation adjacent the return electrode does not exceed the limits mentioned in the introduction hereof. It will now be seen that by a proper selection of such parameters the return electrode is made self-limiting, thereby obviating the need for the additional monitoring circuits to which reference is made above.

To facilitate description of the principles underlying the invention, the foregoing is described in terms of impedances whose principal components are resistances and capacitive reactances. However, the principles of the invention are also applicable to other embodiments in which the impedances include any combination of resistive, capacitive and/or inductive impedances.

The invention hereof is now described in connection with applications in which the self-limiting characteristics of an electrosurgical return electrode are achieved through use of a removable semi-insulating sheet or member and a separate electrically conducting element. The use of the semi-insulating sheet or member converts the separate electrically conducting element, into a functional electrical return electrode with the desired self-limiting characteristics. In the following discussion, the terms "semi-insulating sheet" and "semi-insulating member" are used interchangeably and a discussion of the "sheet" is applicable to the "member," and vice versa.

Figure 4A:
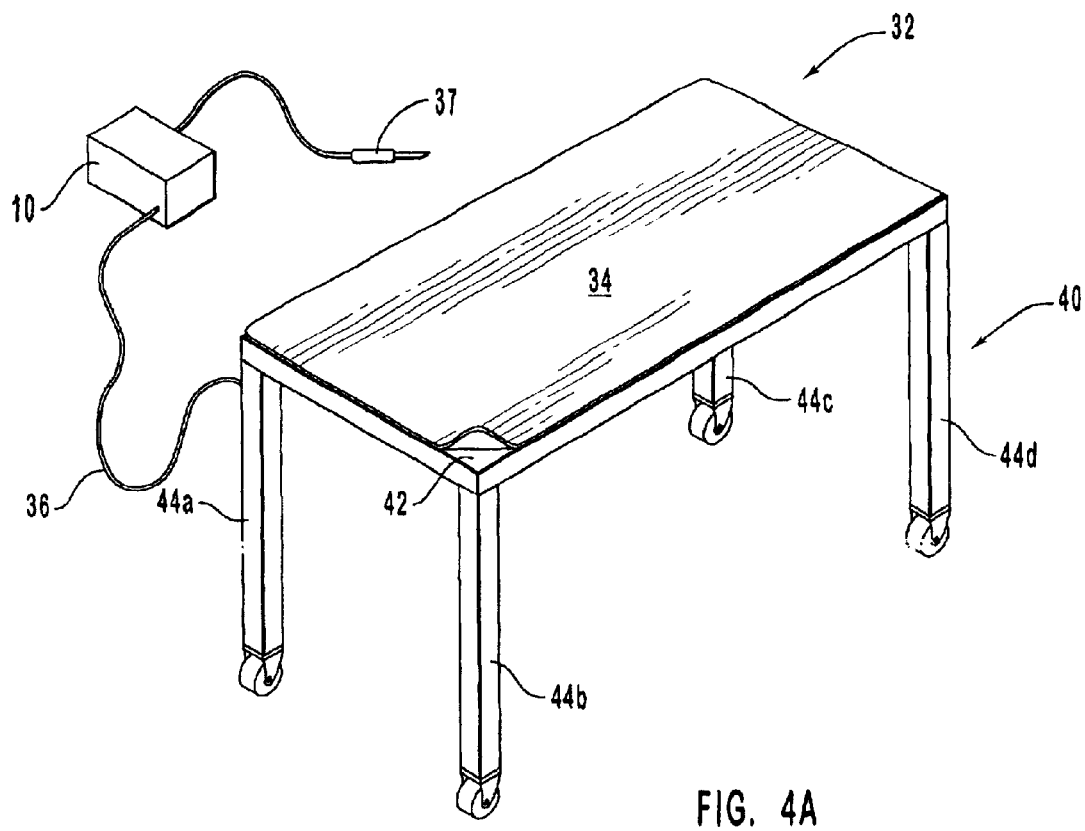
FIG. 4A is a perspective view of an improved electrical return electrode in which the present invention is utilized, illustrating the semi-insulating sheet or member, an electrically conductive work surface, an operating table, and an electrical connector to the electrical surgical generator from the electrically conductive surface.

Reference is now made to FIG. 4A that depicts an exemplary electrical return electrode 32 of one embodiment of the present invention. As illustrated, electrical return electrode 32 includes a semi-insulating sheet 34 that can be removably coupled with an operating table 40, which functions as an electrically conducting element of the electrosurgical return electrode. The semi-insulating sheet 34 of the present invention, either alone or in combination with operating table 40, provides the impedance for the proper functioning of the improved electorsurgical return electrode 32 with the desired self-limiting characteristics. The impedance characteristics of the semi-insulating sheet 34 and the self-limiting characteristics of the electrosurgical return electrode 32 will be described in more detail hereinafter.

According to one embodiment, operating table 40 includes a work or working surface 42. The work surface 42 has electrically conductive characteristics such that work surface 42 and operating table 40 have substantially similar electrical characteristics. Although this is the case in one configuration, it can be understood by one skilled in the art, in light of the teaching contained herein, that work surface 42 and the remainder of operating table 40 have differing electrical characteristics. For instance, work surface 42 can be more or less electrically conductive than the remainder of operating table 40.

FIG. 4A illustrates in perspective operating table 40, which includes conventional legs 44a–44d that may be fitted with wheels or rollers as shown. All or a portion of table 40 can act as the electrically conducting element to be used with semi-insulating sheet 34 to create a self-limiting electrosurgical return electrode. Consequently, table 40 is one structure that is capable of performing the function of an electrically conducting element. Similarly, table 40 is one structure capable of performing the function of means for supporting a patient during treatment. One skilled in the art, in light of the teaching contained herein, however, may appreciate that various other configurations of, an electrically conducting element and means for supporting are applicable. For instance, alternate embodiments of electrically conducting elements include chairs, plates, beds, and carts that are electrically conductive or are imbued with electrically conductive materials, such as but not limited to metallic compositions or surfaces, carbon black, wires, ionic solutions, combinations thereof, or the like. In alternative embodiments, the electrically conducting element is separate from a work surface of table 40 or other suitable means for supporting a patient during treatment. Examples of such a separate electrically conducting element could include a metal sheet, a layer of carbon black, a layer of conductive gel, a mattress filled with ionic solution, wires, combinations thereof, or the like, or any other conductive layer placed between means for supporting a patient and semi-insulating sheet 34.

Table 40, acting as an electrically conducting element, is electrically coupled to an electrosurgical generator 10 via an electrical connector 36. Table 40 and electrical connector 36 provide the electrical connection for normal functioning of electorsurgical return electrode 32. Stated another way, electrical connector 36 is coupled to table 40, thus providing the electrical connection for current flowing during use of an electrosurgical instrument 37 coupled to electrosurgical generator 10.

Generally, electrosurgical generator 10 generates the electrical current for operation of electrosurgical instrument 37. Various types of electrosurgical generators are known to those skilled in the art, such as but not limited to constant power, voltage, and/or current or variable power, voltage and/or current.

Similarly, various types of electrosurgical instrument are known to those skilled in the art, such as but not limited to, electrosurgical instruments used to cut, cauterize, combinations thereof, or the like to any portion of a patient's body, whether internal or external thereto. For instance, laparoscopic electrodes, electro-surgical pencils, electrosurgical blades.

Furthermore, electrical connector 36 can have various configurations so long as electrical connector 3 electrically connects to table 40, or other appropriate electrically conducting element, and electrosurgical generator 10. For instance, electrical connector 36 can be permanently connected to table 40 and electrosurgical generator 10. Alternatively, electrical connector 36 may be releasably connected to table 40 and electrosurgical generator 10 as with clamps, threaded inserting elements, or an plug capable of transmitting electrical energy, such as but not limited to, a banana plug, a phone jack, an Ethernet jack, a coaxial connector, or the like. Other configurations will be familiar to those skilled in the art in light of the teaching contained herein, such as electrical connector 36 permanently coupled with electrosurgical generator 10, but releasably coupled to table 40, or other appropriate electrically conducting element.

Figure 5:
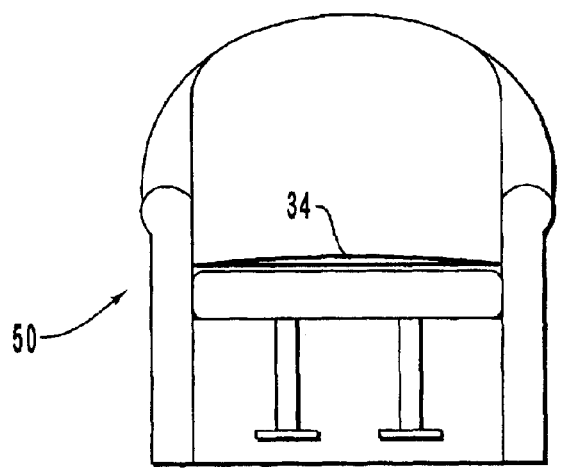
FIG. 5 is a front view illustrating a surgical chair with a semi-insulating sheet or member disposed on the surface of the seat thereof.

In FIG. 4A, the entire upper surface of the table is shown as being covered with semi-insulating sheet 34. In one embodiment, semi-insulating sheet 34 covers the entire work surface 42, where the work surface 42 is made of an electrically conductive material. However, it should be understood that entire coverage is by no means required in order to practice the principles of the invention. When used with conventional electrosurgical generators, return electrode 32 needs only to present an effective working surface area which is sufficient to provide adequate resistive, capacitive, or inductive coupling at the typically employed RF frequencies so as not to interfere with the surgeon's ability to perform surgery while at the same time avoiding undesired tissue damage. It has been found that at conventional electrosurgical frequencies, this has necessitated only an effective working surface area no larger than about the projected outline of one-half of the torso for an adult patient lying on an operating table or the buttocks of a patient sitting in a chair such as is illustrated in FIG. 5. However, the effective working surface area will vary depending on the material used, in some geometrical configurations, and in instances where various layers of operating room linens are placed over the electrode. The principles hereof may be successfully employed and the effective working surface area of the return electrode determined in such circumstances by routine experimentation. Under certain conditions, the effective working surface may be as small as about seven square inches (or about 45 square centimeters).

Moreover, although the semi-insulating sheet 34 as shown in FIGS. 6–8, and 10 are depicted as being rectangular in shape, it will be evident that they could be oval or contoured as, for example, to follow the silhouette of the torso or other principal part of the body of a patient. As will be evident from the foregoing, it is important that semi-insulating sheet 34 be configured so that when return electrode 32 is used: (1) the return current density on the surface of the patient is sufficiently low; (2) the electrical impedance between the electrode, i.e., the combination of semi-insulating sheet 34 and an electrically conductive element, and the patient is sufficiently low so that electrical energy is not concentrated sufficiently to heat the skin of the patient at any location in the electrical return path by more than six degrees (6°) Celsius; and (3) the characteristics of the materials and geometries are such that if the effective area of the return electrode is reduced below a selected threshold level, there will be insufficient energy dissipated at the surgeon's implement for him to continue effectively using the implement in its electrosurgical mode.

As will be recognized by those skilled in the art, it is not necessary for there to be direct ohmic contact between the skin of a patient and the return electrode hereof for the electrode to perform generally according the foregoing description, for although capacitive reactance (represented by the distance between a patient's body and the electrode) will be introduced if something such as a surgical gown separates them, such capacitive reactance will modify rather than destroy the impedance identified as $z_3$.

As is known to those skilled in the art, in an alternating current circuit (e.g., such as those used in electrosurgery) the capacitive reactance of an impedance is a function both of capacitance and the frequency of the alternating current electrical signal presented to the $$X_c = \frac{1}{2\pi f C} \quad (2)$$

reactance. Thus, the formula for capacitive reactance (in ohms) is
where Xc is capacitive reactance in ohms, π is 3.14159, ƒ is frequency in hertz, and C is capacitance in farads. The formula for capacitance in a parallel plate capacitor is:

$$C = \frac{\kappa \varepsilon_0 A}{t} \quad (3)$$

where C is capacitance in Farads, κ is the dielectric constant of the material lying between the effective plates of the capacitor, A is the area of the smallest one of the effective plates of the capacitor in square meters, t is separation of the surfaces of the effective plates in meters, and $\varepsilon_0$ is the permittivity of air in Farads/meter. Thus, it will be seen that to meet maximum permissible temperature rise criteria in an embodiment in which electrode circuit capacitance is substantial, different minimum sizes of electrodes may be used depending upon the frequency of the electrical generator source, the separation of the body of the patient from the electrode, and the material lying between the effective conductive region of the electrode and the adjacent body surface. Accordingly, although the principles of the invention are applicable to a wide range of frequencies of electrosurgical energy, the considerations set forth herein for minimum sizes of return electrodes specifically contemplate frequencies typically employed in conventional electrosurgical energy generators.

Those skilled in the art know that, with the currently used disposable return electrodes, reducing the effective size of the electrode to about three square inches will not reduce the RF current flow to a level where it will impede the surgeon's ability to perform surgery nor concentrate current to a level to cause patient trauma. However, to provide for some spacing of the electrode from patient's body, a return electrode according to the invention hereof, can utilize a minimum effective area of between about 7 and about 11 square inches (about 45 $cm^2$ to about 70 $cm^2$) with a relatively small separation from the skin of the patient such as that provided by a surgical gown or no interposing gown at all. Such an effective area is easy to obtain if the patient is positioned on an electrode that is the size of their upper torso or larger.

The characteristics of the desired dielectric for the present embodiment are sufficiently comparable to those of selected rubbers, plastics and other related materials that the latter may be satisfactorily employed as materials for semi-insulating sheet 34. As mentioned above, with semi-insulating sheet 34, if the patient is positioned such that not enough of the semi-insulating sheet 34 is in close proximity to the patient to result in the desired low impedance, the result would be that the current flow from the electrosurgical generator would be reduced to a level making it difficult for the surgeon to perform surgery. Thus, in the present embodiment, notwithstanding interposition of some additional capacitance represented by a surgical gown, the features described herein will continue to occur.

Figure 4B:
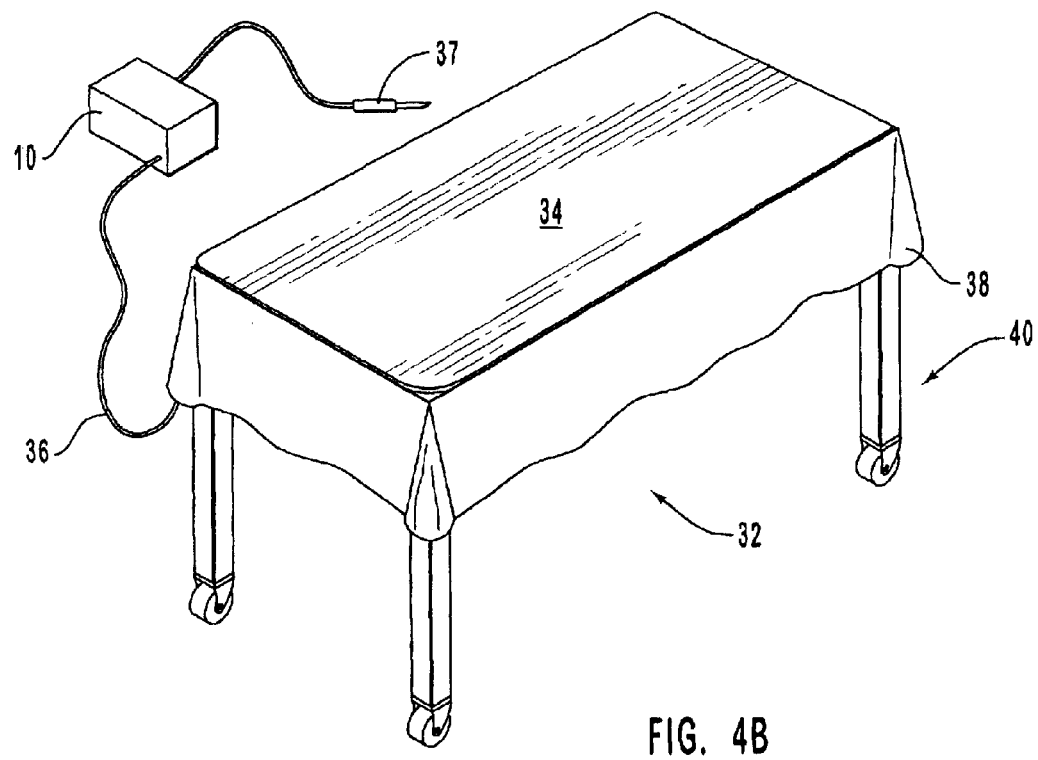
FIG. 4B is a perspective view of an improved electrical return electrode, illustrating the semi-insulating sheet or member, and the protective flange for preventing inadvertent contact with the electrically conducting element.

Referring now to FIG. 4B, depicted is another alternate embodiment of semi-insulating sheet, referenced by numeral 34b. As illustrated, semi-insulating sheet 34b can include a protective flange 38. The protective flange 38 is used to cover portions of table 40 acting as an electrically conducting element and/or work surface 42 of table 40 with which the patient or the user could come in contact. By covering such portions of surface 42 and table 40, protective flange 38 ensures that current will flow through electrosurgical return electrode 32. The self-limiting characteristics of return electrode 1 ensure that current density flowing from the patient or the user is at safe levels.

Figure 11:
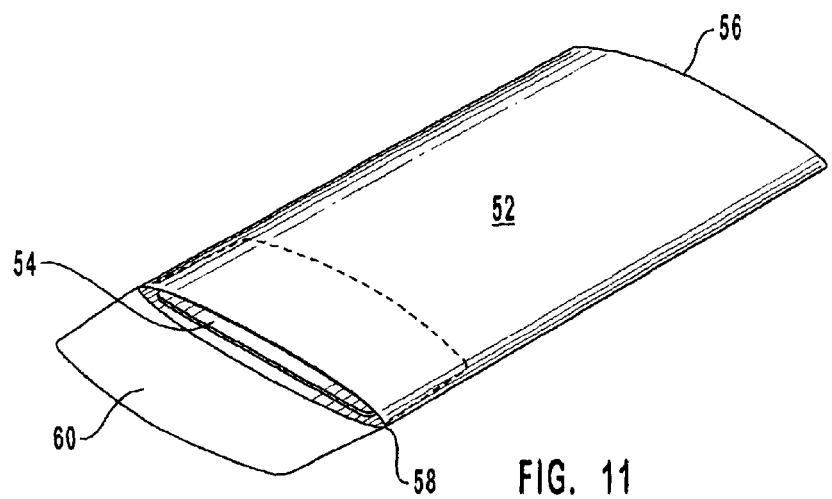
FIG. 11 is a perspective view of a sleeve or cover adapted for encasing an electrically conducting element of the present invention.

In another embodiment, as illustrated in FIG. 11, the semi-insulating sheet has the form of an envelope and is adapted to receive an electrically conducting element within the interior of the envelope, as will be described hereinafter. In another embodiment, a protective flange 38 is coupled to semi-insulating sheet 34. In alternative embodiments protective flange 38 includes a separate covering for enveloping working surface 42 and any appended electrically conducting elements, such as the legs of a table as shown in FIG. 4B. In yet another embodiment, protective flange 38 is coupled to a disposable, reusable, or washable protective sleeve used to cover semi-insulating sheet 34.

As mentioned above, FIG. 5 is a front view illustrating a surgical chair 50 with a semi-insulating sheet 34 according to the invention disposed on the upper surface of the seat thereof. Consequently, surgical chair 50 and semi-insulating sheet 34 collectively form an electrosurgical return electrode. Illustratively, surgical chair 50 as a whole or a portion thereof can be configured to act as the electrically conducting element of the present invention. Accordingly, when a patient is sitting in the chair, the buttocks and upper part of the thighs overlie and are in sufficiently close proximity to semi-insulating sheet 34 so that coupling there between presents an impedance meeting the foregoing criteria; namely, that the electrical impedance between semi-insulating sheet 34 and/or all or a portion of surgical chair 50 and the patient is sufficiently low to allow the surgeon to perform the procedure while providing that current density is sufficiently low and that insufficient electrical energy is developed across the return impedance to heat the skin of the patient at any location in the electrical return path by more than six degrees (6°) Celsius.

Figure 6:
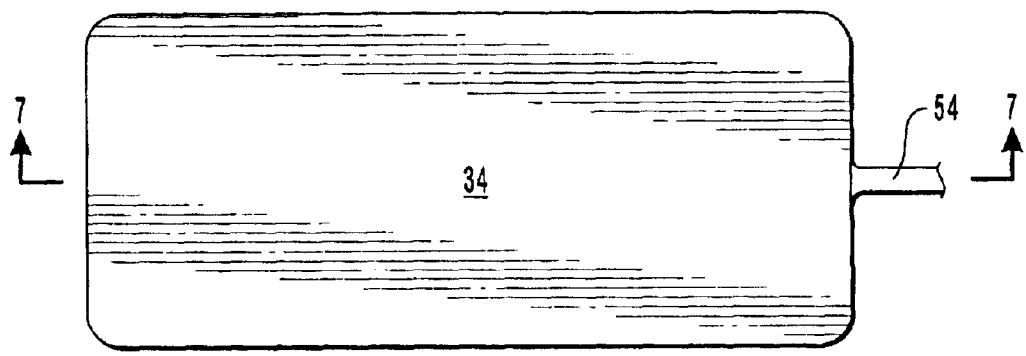
FIG. 6 is a top view of an electrosurgical return electrode illustrating the semi-insulating sheet or member substantially covering the electrically conductive work surface according to the invention.

FIG. 6 is a top view of another semi-insulating sheet according to the invention. It will be observed that the upper exposed, or working, surface of the semi-insulating sheet again is expansive so as to meet the foregoing criteria for low impedance. The semi-insulating sheet can optionally cover the entire surface of an operating table or the entire seat surface of a dental or other patient chair to provide a greater surface area than that of the projected area of the buttocks or torso of a patient so that if a patient moves position during the course of a procedure, a sufficient portion of the patient will remain in registration with the semi-insulating sheet surface, and hence the return electrode, so that the effective impedance will remain less than the above-described level.

At this juncture, it may be helpful to emphasize characteristics of the improved semi-insulating sheet and the return electrode that are deemed particularly relevant to understanding the present invention. First, as mentioned above, the semi-insulating sheet and hence the return electrode does not need to be in direct contact with a patient, either directly or through intervening conductive or nonconductive gel. In addition, because of its expansive size, there is no need for tailoring the semi-insulating sheet and hence the return electrode to fit physical contours of a patient. In this connection, it has been found that although with selected materials and geometries, the self-correcting and self-limiting principles hereof could be achieved in a semi-insulating sheet and hence a return electrode as small as about seven square inches (or about 45 square centimeters) in working surface area, an exemplary range of exposed upper working surface area of the semi-insulating sheet and hence the return electrode lies in the range of from about 11 to 1,500 square inches (or about 70 to 9,680 square centimeters). By making the semi-insulating sheet and hence the return electrode several times larger (typically, at least an order of magnitude larger) in working surface area than previous proposals, the need for direct physical attachment, either directly to the skin of the patient or through gels, is eliminated.

The semi-insulating sheet 34 according to the invention hereof, as illustrated in FIG. 6, may be made of plastic, rubber, or other flexible material which, when used with the electrically conducting element forms a return electrode with an effective dc resistance presented by each square centimeter of working surface of the semi-insulating sheet to be greater than about 8000 Ω. Silicone or butyl rubber has been found to be particularly attractive materials as they are flexible, as well as readily washable and sterilizable. Alternatively, the main body of semi-insulating sheet 34 may be made of inherently relatively high resistance flexible material altered to provide the requisite conductivity. One example of the latter is that of silicone rubber material in which there are impregnated conductive fibers, such as carbon fiber, or in which there have been distributed quantities of other conductive substances such as carbon black, quantities of gold, silver, nickel, copper, steel, iron, stainless steel, brass, aluminum, or other conductors.

Figure 7:
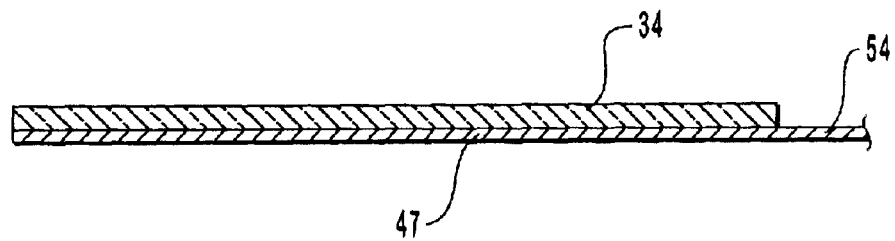
FIG. 7 is a section taken along the lines 7—7 of FIG. 6.

Further reference to FIGS. 6 and 7, reveal the presence of a conventional electrical connector 54 attached to an electrically conducting element 47 of the return electrode to provide a conventional electrical return to electrosurgical radio frequency energy source such as electrosurgical energy source 10 (FIG. 1). Connector 54 is another structure capable of performing the function of connecting means for making electrical connection to the electrode and/or the electrically conducting element. Connector 54 is only illustrative of one possible structure for performing the desired function; it being appreciated by one skilled in the art that various other structures are capable of performing the identified function.

As mentioned above, FIG. 7 is a section taken along the lines 7—7 of FIG. 6. FIG. 7 shows an electrosurgical return electrode 46, similar to electrode 20 of FIGS. 2A–2C, except that electrode 46 is shown separated into semi-insulating sheet 34 and an electrically conducting element 47. Optionally, electrically conducting element 47 can be a thin highly conductive lower stratum that is electrically coupled and removable from semi-insulating sheet 34. This lower stratum can be used to facilitate conduction of current outwardly to an electrosurgical radio frequency energy source. In one exemplary form, the thickness of the semi-insulating sheet 34 lies in a range from about 1/32 inch to 1/4 inch (about 0.08 cm to 0.64 cm), which, with the aforementioned range of impedance of the material forming semi-insulating sheet 34 and/or electrically conducting element 47 and/or the capacitive reactance of the semi-insulating sheet 34, provides the impedance together with desired physical flexibility for ease of use and handling.

In one embodiment of the present invention, the materials and electrode geometries of the semi-insulating sheet 34 are selected so as to prevent creation of pressure sore or decubitus ulcers on a patient resting upon the electrode as disclosed in pending U.S. patent application Ser. No. 09/773,282 filed Jan. 31, 2001 and entitled "Pressure Sore Pad Having Self-limiting Electrosurgical Return Electrode Properties and Optional Heating/Cooling Capabilities," of which the present application is a continuation-in-part and which is incorporated herein by reference. In alternative configurations, the electrosurgical electrode can heat and/or cool the patient during the performance of a surgical procedure.

Figure 8:
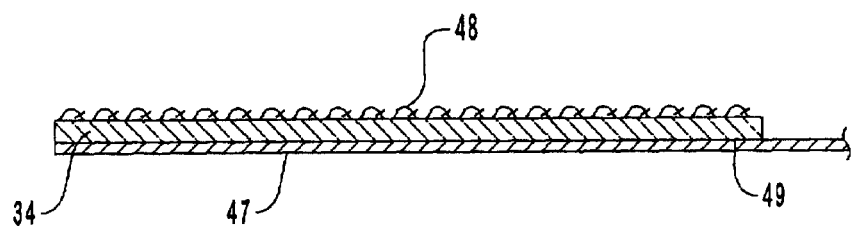
FIG. 8 is a section similar to that of FIG. 7 but illustrating the capacitance presented by a patient's surgical gown.

FIG. 8 is a section similar to that of FIG. 7, but presenting a multiple layer embodiment illustrating the separation presented by a patient's gown according to the invention hereof. There, in FIG. 8 are shown semi-insulating sheet 34 and an overlying effectively capacitive layer 48 representing an insulating dielectric layer, a patient's surgical gown, an operating room linen, a protective sleeve or sheath for the semi-insulating sheet 34, or any combination thereof. It should be understood that in addition to a construction similar to that of the electrode of FIGS. 6–7, electrically conducting element 47 of FIG. 8 could consist of a sheet, plate, or screen of gold, brass, aluminum, copper, silver, nickel, steel, stainless steel, conductive carbon, conductive fluids, gels, saline, and the like that can be rested upon another structure, such as a grounded table, chair, or the like. Further reference to FIG. 8 reveals that embodiments of the present invention can facilitate the inclusion of another dielectric layer 49 covering the lower surface of semi-insulating sheet 34.

Figure 9:
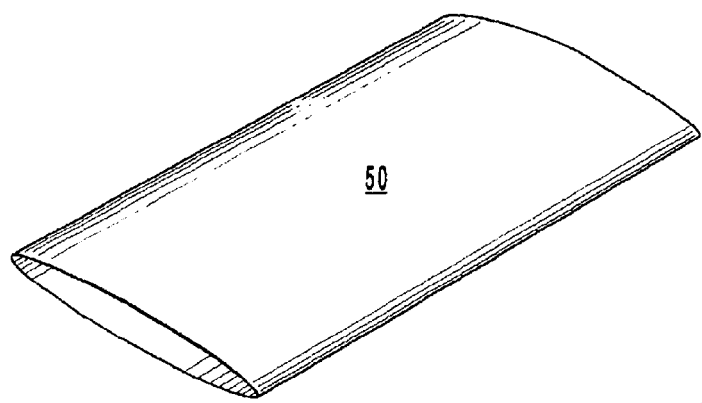
FIG. 9 is a perspective view of a sleeve or cover adapted for encasing any of the embodiments of FIGS. 6–8.

FIG. 9 is a perspective view of a sleeve 50 adapted for encasing any one of the embodiments of FIGS. 6–8. Thus, provision is optionally made for encasing the foregoing semi-insulating sheet 34 within protective envelopes in situations in which it is desired to eliminate the need for cleaning semi-insulating sheet 34 itself by protecting it from contamination through the use of a sleeve of impervious material from which semi-insulating sheet 34, after use, can merely be withdrawn and the sleeve discarded. As will be evident to those skilled in the art, such a sleeve may be made of any of a variety of known materials, such as vinyl plastics, polyester or polyethylene.

Figure 10:
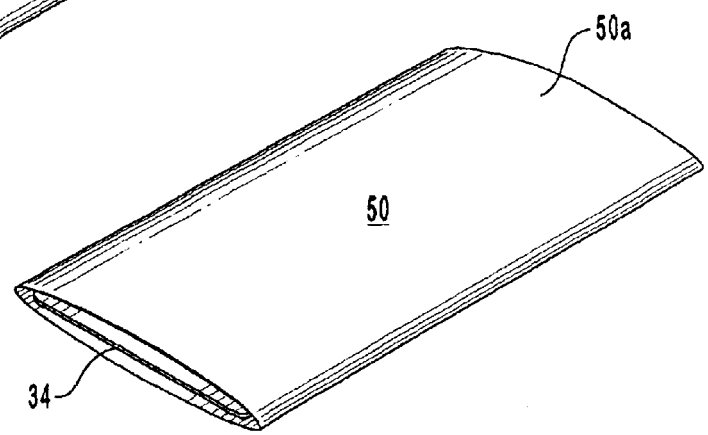
FIG. 10 is a view illustrating one of the embodiments of FIGS. 6–8 encased within the sleeve or cover of FIG. 9.

FIG. 10 is a view illustrating semi-insulating sheet 34 encased within the sleeve of FIG. 9. There, it will be seen, is outer surface 50a of sleeve 50; and shown encased within sleeve 50 for illustrative purposes is semi-insulating sheet 34 of FIG. 6.

In another embodiment, as illustrated in FIG. 11, a sleeve 52 functions as semi-insulating sheet 34 and receives within an interior portion of sleeve 52 an electrically conducting element, referenced by numeral 54. In this manner, semi-insulating sheet 34 completely or partially surrounds the electrically conducting element and prevents inadvertent contact of the patient, physician, or other individual associated with the electrosurgical procedure with the electrically conducting element.

As shown, sleeve 52 has a first end 56 and a second end 58. First end 56 is open to allow placing of electrically conducting element 54 into an interior of sleeve 52. Disposed at second end 58 is a flap 60 that is adapted to be at least partially located within the interior of sleeve 52, as shown by dotted lines, to cover the end of electrically conducting element 54 and prevent inadvertent contact with the patient, physician, etc. Flap 60 is one structure capable of performing the function of means for closing an end of the sleeve. One skilled in the art can identify various other configurations of means for closing an end of the sleeve. For instance, a flap can include a removable adhesive adapted to removably couple the flap to the outer surface of sleeve 52. In still another configuration, the outer surface of sleeve 52 includes a portion of a hook and loop fastener, with a portion of the flap having a complementary portion of the hook and loop fastener. In another configuration, the sleeve is devoid of a flap and an end of the sleeve is closed using zip type fastener, hook and loop type fastener, or the like. Still in another configuration, the sleeve has an elongated form so that a portion of the sleeve can be folded into contact with the outer surface of the sleeve to prevent inadvertent contact with the electrically conducting element.

One skilled in the art can identify various other configuration of the sleeve. For instance, the sleeve can be open at both the first end and the second end, with the ends being closed by appropriate means for closing an end of the sleeve. In another configuration, the sleeve includes an opening between a first end and a second end, with the first end and second end being closed. This opening can be closed though one or more of the various means for closing disclosed herein or otherwise known to one skilled in the art in light of the teaching contained herein.

Total Electrode Ground Pad Impedance and Self-Limiting Feature

Figure 12:
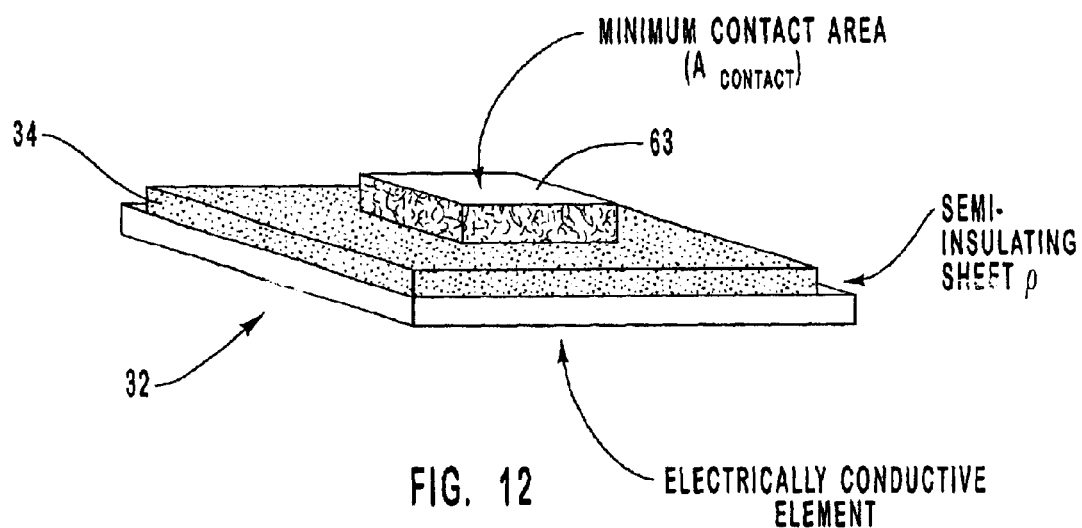
FIG. 12 is a perspective view of an electrode according to the invention illustrating a simulated condition when the effective contact area with a patient is substantially less than the physical electrode size.

FIG. 12 depicts an electrosurgical electrode 32 that includes a semi-insulating sheet 34 and an electrically conducting element 61; the structure and functionality discussed previously with respect to other electrically conducting elements applies to electrically conducting element 61. The electrode 32, and more specifically, semi-insulating sheet 34, is in contact with another conducting layer 63, which represents a patient thereupon. The self-limiting feature of electrosurgical return electrode 32 (maintains current densities below a threshold level) arises due to the total impedance of electrode 32, whether such impedance arises from semi-insulating sheet 34 alone or in combination with electrically conducting element 61 and/or conducting layer 63. Furthermore, the total impedance may arise from the various resistive, inductive, and/or capacitive components of electrically conducting element 61, semi-insulating sheet 34 and/or conducting layer 63.

Electrode 32, which includes a semi-insulating sheet 34 having a bulk resistivity $\rho$ and thickness t. An area A placed between a conductive surface, i.e., electrically conducting element 61, and the patient may be modeled as a resistor (R) in parallel with a capacitor (C).

For ease of explanation, we will determine the resistive requirements of electrode 32 for self-limiting in a purely resistive scenario where electrode 32 is modeled as a resistor in parallel with a capacitor. Following the calculation of the minimum requirements for self-limiting in the purely resistive case, we will generalize the analysis for any impedances, whether such impedances result from resistive, capacitive, and/or inductive components.

As such, the resultant total impedance equivalent for the resistor in parallel with the capacitor combination is $$Z_{tot} = R \| X_C = \frac{(R)\left(\frac{1}{j\omega C}\right)}{(R) + \left(\frac{1}{j\omega C}\right)} = \frac{R}{1 + j\omega CR} \quad (4)$$

where j is an imaginary component of reactance, and $\omega$ is the angular frequency and is defined as $\omega = 2\pi f$ where f is the electrosurgical generator frequency. The magnitude of the impedance is $$|Z_{tot}| = \sqrt{\frac{R^2}{1 + \omega^2 C^2 R^2}} = R\sqrt{\frac{1}{1 + \omega^2 C^2 R^2}} \quad (5)$$

Substituting the dependence of R and C on the area A, thickness t, bulk resistivity $\rho$, and the dielectric constant of the material $\kappa$ defined by $$R = \frac{\rho t}{A} \quad (6)$$

and $$C = \frac{\kappa \varepsilon_0 A}{t} \quad (7)$$

where electric permittivity constant $\epsilon_0 = 8.85 \times 10^{-12}$ F/m, the magnitude of the total impedance is given by $$|Z_{tot}| = \frac{\rho t}{A} \sqrt{\frac{1}{1 + \omega^2 \left(\frac{\kappa \epsilon_0 A}{t}\right)^2 \left(\frac{\rho t}{A}\right)^2}} = \frac{\rho t}{A} \sqrt{\frac{1}{1 + \omega^2 \kappa^2 \epsilon_0^2 \rho^2}} \quad (8)$$

According to the AAMI standard, the total impedance of the electrosurgical electrode should be less than 75Ω under normal operating conditions. Therefore, in one configuration, $$\frac{\rho t}{A} \sqrt{\frac{1}{1 + \omega^2 \kappa^2 \epsilon_0^2 \rho^2}} \leq 75\Omega \quad (9)$$

We define β as $$\beta = \frac{Z_{tot}}{75\Omega} \quad (10)$$

If β<<1, the electrode will have very low impedance compared to the AAMI standard, and the surgeon will not notice any degradation in the electrosurgical cutting power due to the electrode. If: β>>1, the electrosurgical electrode will have such a large impedance that the surgeon will no longer be able to perform electrosurgery. Using β in the above inequality, the expression becomes an equality:

$$\frac{\rho t}{A} \sqrt{\frac{1}{1 + \omega^2 \kappa^2 \epsilon_0^2 \rho^2}} = 75\beta \quad (11)$$

In one configuration, self-limiting occurs when the electrode has a large electrode area in contact with the patient (FIG. 16), i.e., a large surface area of semi-insulating sheet 34 is in contact with the patient; however, in one exemplary embodiment it is also desirable for self-limiting to occur when the patient only makes contact with a small fraction of the total semi-insulating sheet 34 area (FIG. 12). For self-limiting to work properly, the current density (I/A), where I is the total current through the contact area A of semi-insulating sheet 34 and the electrosurgical return electrode, for an exemplary electrodes does not exceed a critical value $$\left(\frac{I}{A}\right) \leq \left(\frac{I}{A}\right)_{critical} = 100 \text{ mA/cm}^2 \quad (12)$$

AAMI standards indicate that normal electrosurgical currents are on the order of 500–700 mA. If we set 1000 mA=$I_{max}$ as a safe upper limit as to what one might expect for an above average power surgery, then, in order to return the current to the electrode without exceeding $I_{critical}$, the contact area $A_{contact(min)}$ for traditional electrosurgical return electrodes must have a minimum size:

$$A_{contact(min)} \geq \frac{I_{max}}{\left(\frac{I}{A}\right)_{critical}} = \frac{1000 \text{ mA}}{100 \text{ mA/cm}^2} = 10 \text{ cm}^2 \quad (13)$$

It can be appreciated that $I_{max}$ may vary from patient to patient due to changes in the amount of time that the electrode is in contact with the patient, the electrical characteristics of the patient's skin (i.e., resistivity, and the like), the amount of heat being conducted by the patient, the patients initial skin temperature, and the like. With an electrosurgical return electrode designed according to the prior art, in the event that the contact area with the patient reduces below the $A_{contact(min)}$, while maintaining the $I_{max}$, a burn may result because $(I/A)_{critical}$>100 mA/cm², which is the burn threshold. In contrast, the present invention limits the possibility of a burn caused from a reduction of the contact area below $A_{contact(min)}$, while also preventing electrosurgical procedures when the contact area is significantly reduced. Therefore, by selecting the appropriate impedance of the electrosurgical return electrode, the current I is always reduced below $I_{max}$ when A<$A_{contact(min)}$.

Figure 13:
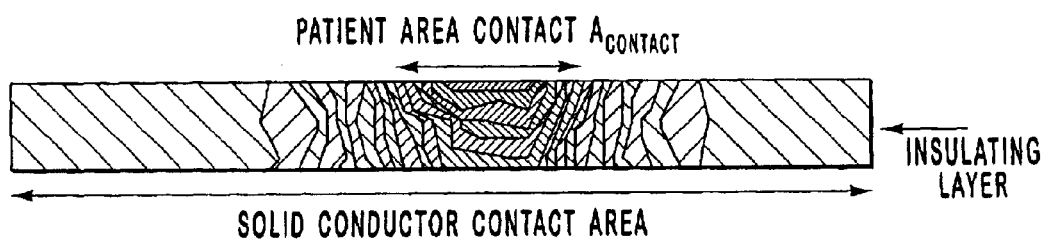
FIG. 13 is a view illustrating current flow density within the electrode when the effective patient contact area is much smaller than the total electrode area.

As such, the impedance between the small electrode with area $A_{contact(min)}$ and the larger metal foil is not simply $$R = \frac{\rho t}{A_{contact(min)}} \quad (14)$$

as current can flow through the areas not directly below the patient contact area $A_{contact(min)}$ (FIG. 13). Approximately 10–20% more current flows through the patient contact area $A_{contact}$ than one would expect if the total area of the semi-insulating sheet 34 were $A_{contact(min)}$. Equivalently, the effective impedance of the electrode is 10–20% less than what one would normally expect if these edge effects were not present resulting in additional current flow.

As previously mentioned, FIG. 13 reveals current flow distribution through the semi-insulating sheet 34 of the electrode when the upper contact area with the patient is much smaller than the total electrode surface area. As depicted, current flows through parallel paths around the contact region thus reducing the overall impedance to current flow and thereby increasing the effective area about 10–20 percent. In the Figure, the opaque or heavily hatched region denotes heavier current flow, and the lighter or lightly hatched region denotes lesser current flow.

In order for the electrode to be self limiting, which is efficacious as defined by the AAMI standard, $A_{contact(min)}$ can have a value from about 7 cm² to about 22 cm², and in one configuration about 10 cm² for electrosurgical currents between 100 mA and about 2,000 mA. Similarly, β can range from about 10 to about 50, and in one configuration have a value of about 10. Using the various values for $A_{contact(min)}$ and β, it is possible to solve Equation 11 for the thickness t as a function of the bulk resistivity ρ at different electrosurgical generator frequencies ω, while inserting a factor of 1.2 to account for the edge effects described above. In the particular illustrative embodiment discussed herein, the factor of 1.2 is included within the resistivity and reactance terms of the equation; however, it may be appreciated by one skilled in the art that the factor of 1.2 is geometry dependent for both the resistive and reactance terms and may vary. Additionally, the value of 1.2 is based on the illustrative geometry of the presently described self-limiting electrode and may vary as the geometry of the electrode varies to account for the different edge effects.

The resulting equation (which identifies and defines the interrelationships of parameters affecting self-limitation) is $$t = \frac{1.2 \, A(75 \, \beta) \sqrt{1 + \omega^2 \rho^2 \kappa^2 \epsilon_0^2}}{\rho} \quad (15)$$

Figure 14:
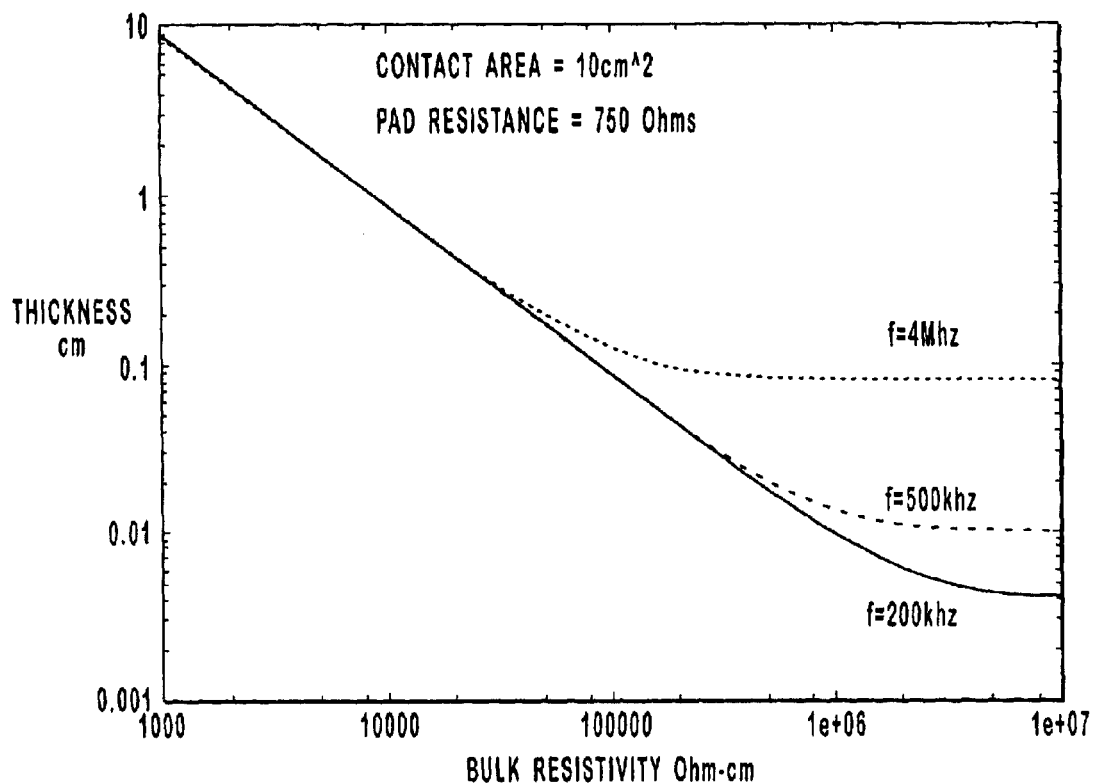
FIG. 14 is a graph depicting variations of bulk resistivity of the semi-insulating sheet or member as a function of semi-insulating sheet or member thickness for different electrosurgical generator frequencies.

Using Equation 15, FIG. 14 illustrates the variation of minimum bulk resistivity, with semi-insulating sheet 34 thickness, requiring κ=5. The maximum semi-insulating sheet 34 thickness one could imagine using would range from about 0.5 to about 4 inches (about 1.3 cm to about 10.2 cm) and in one configuration about 1 inch thick (about 2.5 cm). Above these thicknesses, the semi-insulating sheet 34 may become unwieldy to use and uncomfortable for the patient. Thus, to be self-limiting, the minimum bulk resistivity for an electrode of such thickness is about 4000 Ω·cm.

The preceding equations and discussion are representative of the bulk resistivity for the electrosurgical electrode to be self-limiting. It may be appreciated, however, that the above analysis may be repeated to obtain the self-limiting impedances for electrodes modeled using primarily capacitive or inductive components, or combinations of resistive, capacitive, and/or inductive components. Therefore, following is a discussion of the self-limiting requirements for the bulk impedance of the electrosurgical electrode, whether such impedance arises from resistive, capacitive, and/or inductive components of impedance.

Other Exemplary Embodiments

The self-limiting behavior of the electrosurgical electrode of the present invention results from the existence of sufficient return impedance to make an electrode site burn impossible when the area of contact between the patient and the electrosurgical return electrode is substantially reduced. As shown above, the combination of the maximum electrosurgical currents of 1000 mA coupled with the requirement that the current density be kept below 100 mA/cm² yields a minimum safe contact area of 10 cm².

In general, this requirement can be met with any number of electronic components hooked together in various configurations, including series and parallel combinations of capacitors, resistors, and even inductors, provided that the total impedance presented by the resulting circuit be about 75β or greater when the contact area is reduced to 10 cm².

Define the total impedance of the circuit between the return electrode, i.e., the removable semi-insulating sheet 34 and electrically conducting element 61, of the electrosurgical generator and the patient as $Z_{TOT}$. This impedance is generated by the capacitive, resistive, and inductive properties of the materials inserted between the patient and the return electrode. We define the "bulk impedance" of the material η, a volume independent measure of the impedance of the material forming semi-insulating sheet 34, that is frequency dependent, as:

$$\eta = \frac{(A)(Z_{TOT})}{t} \quad (16)$$

Here A is the area of the material and t is the thickness. This is analogous to the relationship between the volume dependent ohmic resistance R and the related volume independent characteristic of the resistive material called the "bulk resistivity" ρ described earlier.

One manner to describe the self-limiting requirement is expressed in terms of η:

$$|Z_{TOT}| = \frac{t|\eta|}{A} > 75\beta \quad (17)$$

Or therefore $$|\eta| > \frac{(75\beta)A}{t} \quad (18)$$

For the previous case (minimum bulk resistivity specification) we used $A = A_{contact(min)} = 10$ cm², (about 1.5 inch²), β=10, and t=$t_{max}$=1 inch (about 2.5 cm), and a factor of 1.2 to account for edge effects to find that for a pure resistive electrosurgical electrode, $$|\eta| > 4000 \, \Omega\cdot\text{cm} \quad (19)$$

Therefore, in the purely resistive case, the bulk impedance (η) is identified as the bulk resistivity (ρ) of the conducting material in the electrode. The results in Equation 19, however, generalize to all materials and electrical components, including resistive, capacitive, and inductive components, and any combinations thereof. As long as the bulk impedance of the electrosurgical electrode is greater than 4000 Ω·cm, the electrode will be self-limiting, regardless of whether the self-limiting behavior is due to resistive impedance, capacitive impedance, inductive impedance, or any combination of these impedances.

As alternate illustrative examples, one might construct a self-limiting electrosurgical electrode using a conductive/resistive return plate coated with an insulating (dielectric) material or one might construct a patient gown out of dielectric material and use a metallic or resistive return electrode. The total effect of these devices would be to create a resistive impedance in series with a capacitive impedance.

For the above defined illustrative examples that model the return electrode in terms of resistive and capacitive impedances, the total impedance of the electrosurgical electrode is the sum of the resistive and the capacitive impedances:

$$Z_{TOT} = R + \frac{1}{j\omega C} \quad (20)$$

In terms of the material bulk resistivity, dielectric constant, area, and thickness, the total impedance is:

$$Z_{TOT} = \frac{\rho t}{A} + \frac{t}{j\omega \kappa \varepsilon_0 A} \quad (21)$$

By multiplying both sides of the equation by the area A, and dividing by the thickness t, we can derive the bulk impedance η:

$$\eta = \rho + \frac{1}{j\omega \kappa \varepsilon_0} \quad (22)$$

The magnitude of the bulk impedance is:

$$|\eta| = \sqrt{\rho^2 + \frac{1}{(\omega \kappa \varepsilon_0)^2}} \quad (23)$$

If we require $$|\eta| > \frac{(75\ \beta)(1.2A)}{t} \quad (24)$$

Then $$\frac{A}{t} < \frac{|\eta|}{1.2(75\ \beta)} = \frac{\sqrt{\rho^2 + \frac{1}{(\omega\kappa\varepsilon_0)^2}}}{1.2(75\ \beta)} \quad (25)$$

As such, the edge effects reduce the bulk impedance of the electrode by about 10–20 percent, thereby causing a corresponding increase in the effective area of the self-limiting electrode by about 10–20 percent, and reducing the possibility of unwanted electrosurgical burns.

Figure 15:
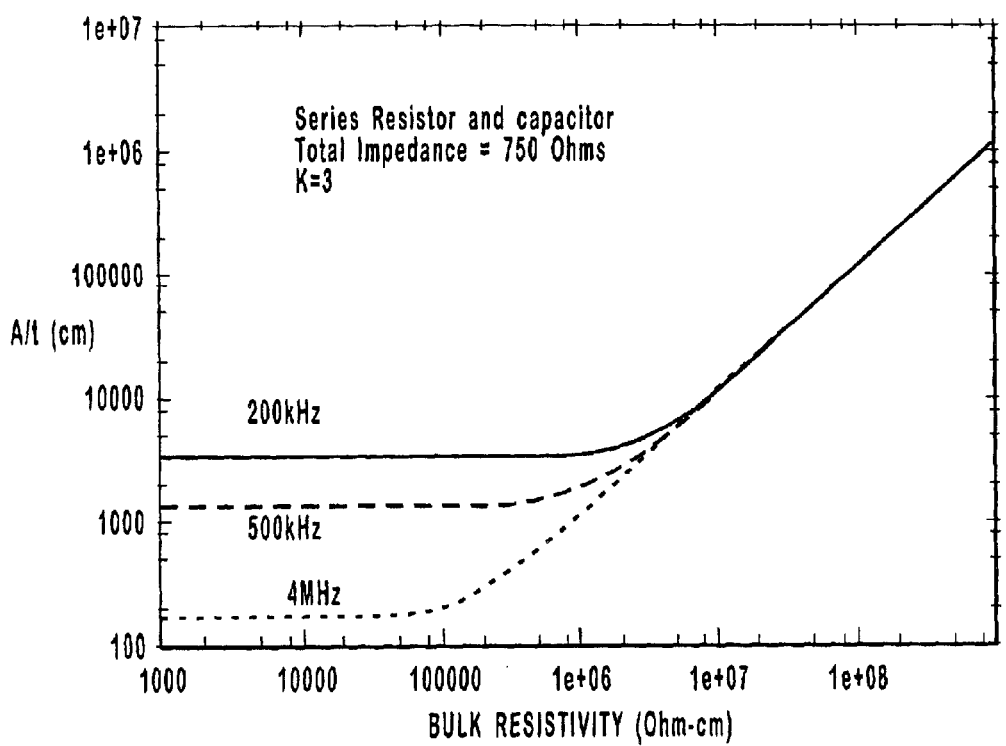
FIG. 15 is a graph showing bulk resistivity as a function of the area divided by the thickness of a semi-insulating sheet or member in accordance with the present invention at various electrosurgical frequencies.

FIG. 15 plots A/t vs. bulk impedance $\eta$ for various electrosurgical frequencies. The y-axis has the minimum ratio of A/t in order to have self-limiting behavior as a function of the bulk impedance. Note that we require bulk impedance always greater than 4000 $\Omega\cdot$cm. On the right hand side of the plot, all of the curves merge into one. In this regime, the total impedance of the circuit is dominated by the resistive component and is, hence, independent of frequency. On the left hand side, the circuit impedance is dominated by the capacitive conduction of current. One requires area to thickness ratios of several hundred to about 10,000 in order to provide sufficient total impedance with the low ohmic resistance in this region.

The resulting lowest possible bulk impedance, therefore, is greater than that anticipated by the Twentier U.S. Pat. No. 4,088,133; and, consequently, the self-limiting electrode according to the invention hereof appears to be neither taught nor suggested by known prior art. A product according to the invention hereof can be easily distinguished from previous art through a simple test of the bulk impedance, such as the bulk resistivity of the insulating material, independent of electrode area or semi-insulating sheet thickness.

Interrelationships of Geometries Materials and Power Sources

As mentioned above, FIGS. 12–18 are set forth to define the geometries and characteristics of materials employed to obtain the foregoing self-limiting action. Discussion will be made hereinafter to present illustrative information and an example related to a semi-insulating sheet configured to create a functional return electrode, when coupled with an electrically conducting element, which may be used for electrosurgical procedures utilizing capacitive conduction, while still remaining self-limiting. Although discussion is made herein with respect to an electrosurgical electrode functioning under capacitive conduction, similar illustrative information and examples may be provided for resistive and inductive conduction, as known by one skilled in the art.

Figure 16:
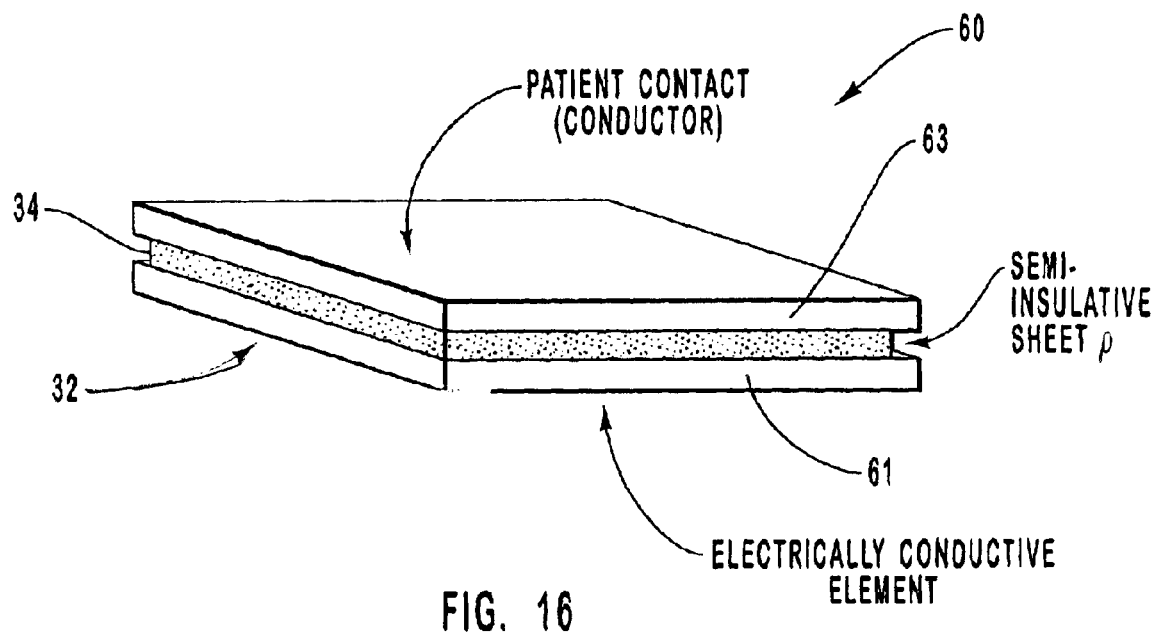
FIG. 16 is a perspective view illustrating, for the purpose of analysis, the circuit equivalent of a patient in operative association with the ohmic and capacitive regions of an electrode according to the invention.
Figure 17:
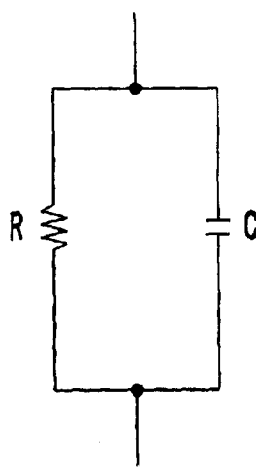
FIG. 17 is a simple electronic schematic circuit equivalent to FIG. 16.

FIG. 16 depicts an electrosurgical electrode 60 including an electrically conducting element 61 and a semi-insulating sheet 34 of material with bulk resistivity $\rho$, thickness t and area A. The semi-insulating sheet 34 is in contact with another conducting layer 63, which represents a patient thereupon. The circuit can be modeled as a resistor R in parallel with a capacitor C (FIG. 17). The resistance R is related to the bulk resistivity $\rho$, area A, and thickness t by the formula $$R = \frac{\rho t}{A} \quad (26)$$

The capacitance C is approximately related to the area A, thickness t, electric permittivity constant $\varepsilon_0 = 8.85 \times 10^{-12}$ F/m and the dielectric constant of the material $\kappa$:

$$C = \frac{\kappa\varepsilon_0 A}{t} \quad (27)$$

The magnitude of the capacitor impedance is $$X_C = \frac{1}{\omega C} = \frac{t}{\omega\kappa\varepsilon_0 A} \quad (28)$$

The ratio Y of the current flow due to the capacitive path to the current flow due to the resistive path is $$Y = \frac{\frac{1}{X_C}}{\frac{1}{R}} = \frac{\frac{\omega\kappa\varepsilon_0 A}{t}}{\frac{A}{\rho t}} = \omega\kappa\varepsilon_0\rho \quad (29)$$

The ratio Y is independent of semi-insulating sheet 34 area and thickness, and more generally, the ration Y is independent of electrode area and thickness. The ration Y is dependent only upon $\kappa$ and $\rho$. For principally capacitive coupling, Y>>1, whereas for principally resistive current, Y<<1. The boundary between the capacitive current and the resistive current is Y=1.

$$1 = 2\pi f \kappa \varepsilon_0 \rho \quad (30)$$

We can use this, along with the value of $\varepsilon_0$, to find the values of $\rho$ for capacitive conduction, given nominal values of $\kappa$ and $\omega = 2\pi f$ where f is the electrosurgical generator frequency.

$$\rho = \frac{1}{2\pi f \kappa \varepsilon_0} \quad (31)$$

For most insulating materials, $\kappa$ ranges from 3 to 5. Commercially available electrosurgical generators presently have operating frequencies ranging from 200 kHz to 4 MHz. For $\kappa=5$ and f=4 MHz, in one configuration $\rho > 1 \times 10^5$ $\Omega\cdot$cm for the electrosurgical electrode to return the majority of its current through capacitive coupling. For $\kappa=3$ and f=200 kHz, we require $\rho > 3 \times 10^6 \Omega\cdot$cm.

The percentage of total current derived through capacitive coupling is given by $$pct = \frac{\frac{1}{|X_C|^2}}{\frac{1}{|R|^2} + \frac{1}{|X_C|^2}} = \frac{|R|^2}{|R|^2 + |X_C|^2} = \frac{\left(\frac{\rho t}{A}\right)^2}{(\rho t)^2 + \left(\frac{t}{A\varepsilon_0\kappa\omega}\right)^2} \quad (32)$$

$$= \frac{\rho^2}{\rho^2 + \left(\frac{1}{\varepsilon_0\kappa\omega}\right)^2} = \frac{(\varepsilon_0\kappa\omega\rho)^2}{(\varepsilon_0\kappa\omega\rho)^2 + 1}$$

Figure 18:
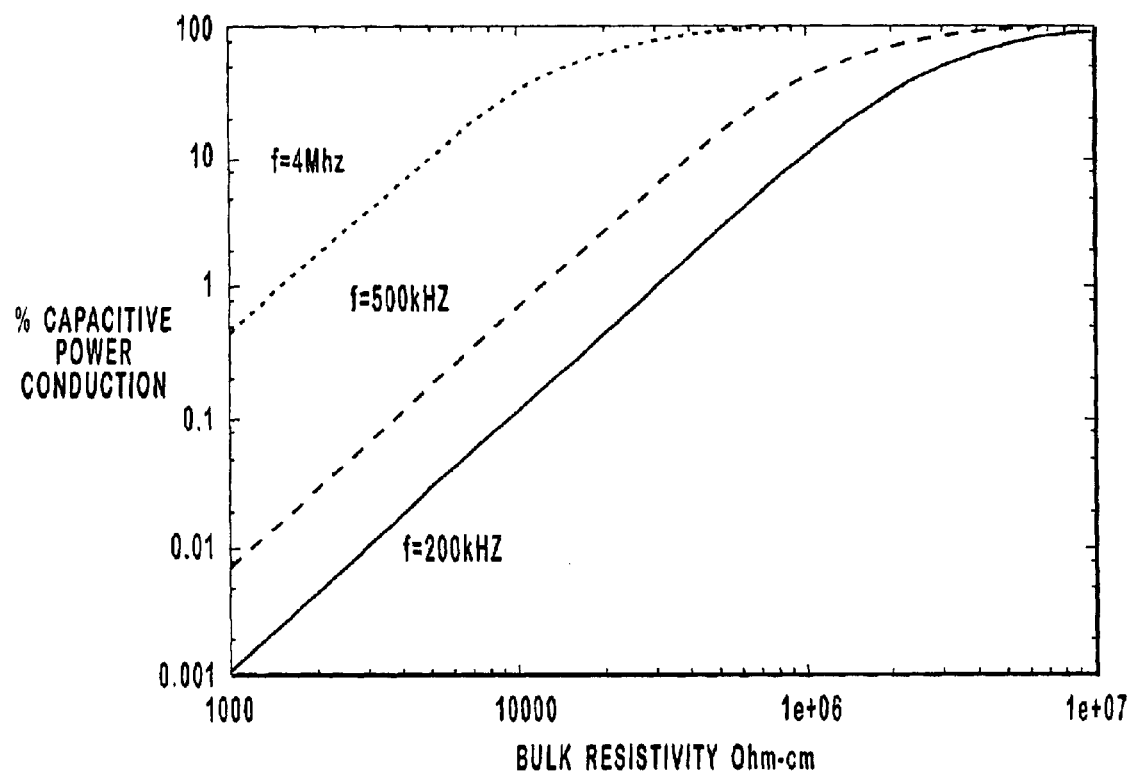
FIG. 18 is a graph depicting percent capacitive power conduction as a function of bulk resistivity of the semi-insulating sheet or member for different electrosurgical operating frequencies.

FIG. 18 illustrates the percentage (%) of capacitive coupling for various frequency electrosurgical generators. At the extreme (4 MHz), a minimum bulk impedance of $10^5$ $\Omega\cdot$cm is used for the majority of the current to be passed through capacitive coupling.

It will now be evident that there has been described herein semi-insulating sheet 34 for use in an improved electrosurgical return electrode characterized by being generally electrode-shaped and evidencing the features of being self-limiting, when used to create a functional electrode, while being reusable, readily cleanable and obviating the necessity for use of conducting gels or supplementary circuit monitoring equipment.

Although the invention hereof has been described by way of exemplary embodiments, it will be evident that adaptations and modifications may be employed without departing from the spirit and scope thereof.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency are to be embraced within their scope.

What is claimed is:

1. A semi-insulating member for use with a separate conducting element to provide a return path for electrosurgical current used in electrosurgery, the separate conducting element being electrically coupled to an electrosurgical generator, the member comprising:

a sheet of material enclosed by an insulating sleeve, said sheet with said insulating sleeve having an effective bulk impedance equal to or greater than about 4,000 Ω·cm when said insulating sleeve is substantially in contact with at least a part of the separate conducting element such that the combination of said sheet, said insulating sleeve, and the separate conducting element are self-limiting so that the electrosurgical current is limited to safe thresholds so as to prevent an undesirable patient burn at a contact area between a patient and said sheet, said insulating sleeve, or the separate conducting element in the event of an accidental reduction in the contact area below a threshold level.

2. The member according to claim 1, wherein said effective bulk impedance of said sheet enclosed by said sleeve comprises at least one electrical component selected from the group consisting of a resistive component, a capacitive component, and an inductive component.

3. The member according to claim 1, wherein said sheet enclosed by said sleeve comprises a layer of dielectric material having a defined capacitive reactance, said sheet and said sleeve being adapted to contact and overly the conducting element when in use.

4. The member according to claim 1, wherein said sheet enclosed by said sleeve comprises a layer of electrically conducting material having a designed bulk impedance equal to or greater than about 4,000 Ω·cm when said sleeve is substantially in contact with at least a part of the separate conducting element.

5. The member of claim 1, wherein said sheet enclosed by said sleeve comprises a working surface configured to be positioned in contact with or in close proximity to a patient.

6. The member of claim 1, wherein said sheet is reusable.

7. A member according to claim 1, wherein said sheet enclosed by said sleeve has a predetermined thickness and wherein the relationship between the bulk impedance, the surface area, and the predetermined thickness of said sheet enclosed by said sleeve when said sleeve is substantially in contact with at least a part of the conducting element are defined by the equation:

$$t = \frac{1.2A(75)\beta\sqrt{1 + \omega^2\eta^2\kappa^2\varepsilon_0^2}}{\rho}$$

where t=thickness (cm)
κ=dielectric constant of insulating material
β=total impedance divided by the AAMI standard (75 ohms)
ω=angular frequency of electrosurgical generator (radians/sec)
η=bulk impedance (Ω·cm)
A=sheet area (cm²)
ε₀=electrical permittivity constant (F/cm).

8. A member for use with a separate conducting element to provide a return path for electrosurgical current used in electrosurgery, the separate conducting element having an electrical connector to an electrosurgical generator and in combination with the member acts as an electrosurgical electrode, the member comprising:

a sheet of material having an effective bulk resistivity equal to or greater than about 4,000 Ω·cm when said sheet of material is substantially in contact with at least a part of the separate conducting element such that the combination of said sheet and the separate conducting element are self-limiting so that the electrosurgical current is limited to safe thresholds so as to prevent an undesirable patient burn at a contact area between a patient and the electrode in the event of an accidental reduction in the contact area below a threshold level, said sheet comprises a layer of dielectric material having at least one of a defined capacitive reactance or a defined inductive reactance, said sheet being adapted to contact and overly the conducting element when in use.

9. A member according to claim 8, wherein said sheet has a predetermined thickness and wherein the relationship between the bulk resistivity, the surface area and the predetermined thickness of the sheet when said sheet of material is substantially in contact with at least a part of the separate conducting element are defined by the equation:

$$t = \frac{1.2A(75)\beta\sqrt{1 + \omega^2\eta^2\kappa^2\varepsilon_0^2}}{\rho}$$

where t=thickness (cm)
κ=dielectric constant of insulating material
β=total impedance divided by the AAMI standard (75 ohms)
ω=angular frequency of electrosurgical generator (radians/sec)
ρ=bulk impedance (Ω·cm)
A=sheet area (cm²)
ε₀=electrical permittivity constant (F/cm).

10. A member according to claim 8, wherein said sheet is adapted to be removably coupled to the conducting element.

11. A removable member for use as a part of an electrosurgical electrode that comprises the removable member and a separate conducting element having an electrical connector to an electrosurgical generator, the removable member comprising:

a sheet of material configured to substantially cover the separate conducting element and having an effective bulk impedance equal to or greater that about 4,000 Ω·cm when said sheet of material is in contact with at least a part of the separate conducting element when a working surface of said sheet is in close proximity to a patient or in contact with the patient without use of a gel.

12. The removable member according to claim 11, wherein the sheet comprises a protective flange.

13. The removable member according to claim 11, wherein the sheet is adapted to enclose the conducting element.

14. The removable member according to claim 11, wherein the sheet has the form of an envelope for enclosing the conducting element.

15. The removable member according to claim 11, wherein the sheet form-fits the conducting element.

16. A removable semi-insulating member comprising a sheet of material configured for use with a separate conducting element as an electrosurgical return electrode, the separate conducting element is electrically coupled to an electrosurgical generator and the sheet of material has an effective bulk impedance equal to or greater that about 4,000 Ω·cm, when said sheet of material is substantially in contact with at least a part of the separate conducting element such that the combination of said sheet and the separate conducting element are self-limiting so that an electrosurgical current is limited to safe thresholds so as to prevent an undesirable patient burn at a contact area between a patient and the electrode in the event of an accidental reduction in the contact area below a threshold level, said sheet comprises a layer of dielectric material having at least one of a defined capacitive reactance or a defined inductive reactance, said sheet being adapted to contact and overly the conducting element when in use.

17. An electrosurgical return electrode having substantially self limiting properties, the electrode comprising:

a conducting element; and a semi-insulating member removably coupled to the conducting element, wherein the conducting element and the semi-insulating member collectively have a bulk impedance equal to or greater than about 4,000 Ωcm when said semi-insulating member is substantially in contact with at least a part of said conducting element such that the combination of said semi-insulating member and the conducting element are self-limiting so that an electrosurgical current is limited to safe thresholds so as to prevent an undesirable patient burn at a contact area between a patient and the electrode in the event of an accidental reduction in the contact area below a threshold level, said semi-insulating member comprises a layer of dielectric material having at least one of a defined capacitive reactance or a defined inductive reactance, said semi-insulating member being adapted to contact and overly the conducting element when in use.

18. The electrosurgical return electrode as recited in claim 17, further comprising means for supporting a patient.

19. The electrosurgical return electrode as recited in claim 17, wherein the semi-insulating member is configured to be substantially in contact with and substantially cover a surface of the conducting element.

20. The electrosurgical return electrode as recited in claim 17, further comprising a means for providing an electrical connection between the conducting element and an electrosurgical generator.

21. The electrosurgical return electrode as recited in claim 17, wherein said semi-insulating member surrounds the conducting element.

22. The electrosurgical return electrode as recited in claim 21, wherein said semi-insulating member is form-fitted to the conducting element.

23. The electrosurgical return electrode as recited in claim 17, wherein the semi-insulating member comprises an interior adapted to receive the conducting element.

24. A semi-insulating member for use with a separate conducting element to provide a return path for electrosurgical current used in electrosurgery, the separate conducting element being electrically coupled to an electrosurgical generator, the member comprising:

a sheet of material having an effective bulk impedance equal to or greater than about 4,000 Ω·cm when said sheet of material is substantially in contact with at least a part of the separate conducting element, wherein said sheet has a predetermined thickness and the relationship between the bulk impedance, the surface area, and the predetermined thickness of said sheet when said sheet of material is substantially in contact with at least a part of the separate conducting element are defined by the equation:

$$t = \frac{1.2 A(75) \beta \sqrt{1 + \omega^2 \eta^2 \kappa^2 \varepsilon_0^2}}{\rho}$$

where t=thickness (cm)

κ=dielectric constant of insulating material

β=total impedance divided by the AAMI standard (75 ohms)

ω=angular frequency of electrosurgical generator (radians/sec)

η=bulk impedance (Ω·cm)

A=sheet area (cm$^2$)

$\epsilon_0$=electrical permittivity constant (F/cm).

25. The member according to claim 24, wherein said effective bulk impedance of said sheet comprises at least one electrical component selected from the group consisting of a resistive component, a capacitive component, and an inductive component.

26. The member according to claim 24, wherein said sheet comprises a layer of dielectric material having a defined capacitive reactance, said sheet being adapted to contact and overly the conducting element when in use.

27. The member according to claim 24, wherein said sheet comprises a layer of electrically conducting material having a designed bulk impedance equal to or greater than about 4,000 Ω·cm when said sheet of material is substantially in contact with at least a part of the separate conducting element.

28. The member of claim 24, wherein sheet comprises a working surface configured to be positioned in contact with or in close proximity to a patient.

29. The member of claim 24, wherein said sheet is reusable.

30. The member of claim 24, further comprising an insulating sleeve adapted to enclose said sheet.

31. The member of claim 24, wherein the sheet comprises an interior adapted to receive the separate conducting element.

* * * * *

UNITED STATES PATENT AND TRADEMARK OFFICE
CERTIFICATE OF CORRECTION

| | |
|---|---|
| PATENT NO. | : 7,166,102 B2 |
| APPLICATION NO. | : 10/142253 |
| DATED | : January 23, 2007 |
| INVENTOR(S) | : Fleenor et al. |

It is certified that error appears in the above-identified patent and that said Letters Patent is hereby corrected as shown below:

Column 2
Line 32, before "Quality", remove [a]

Column 5
Line 64, replace "are" with --is a--

Column 6
Line 43, change "$Z_3$" to --$z_3$--

Column 7
Line 39, change "21 n" to --21n--

Column 10
Line 45, change "3" to --36--

Column 12
Line 50, change both instances of "34b" to --34--

Column 14
Line 30, change "46" to --32--
Line 31, change "46" to --32--

Column 23
Line 41, change "overly" to --overlay--

Column 24
Line 5, change "$\varepsilon$_slectrical" to --$\varepsilon_0$ = electrical--
Line 45, change "bulk impedance" to --bulk resistivity--
Line 46, change "sheet area" to --electrode area--

UNITED STATES PATENT AND TRADEMARK OFFICE
CERTIFICATE OF CORRECTION

PATENT NO. : 7,166,102 B2
APPLICATION NO. : 10/142253
DATED : January 23, 2007
INVENTOR(S) : Fleenor et al.

It is certified that error appears in the above-identified patent and that said Letters Patent is hereby corrected as shown below:

Column 25
Line 22, change "overly" to --overlay--

Signed and Sealed this

Fifth Day of August, 2008

JON W. DUDAS
*Director of the United States Patent and Trademark Office*